US010294481B2

(12) United States Patent
Stephanopoulos et al.

(10) Patent No.: US 10,294,481 B2
(45) Date of Patent: May 21, 2019

(54) MICROBIAL PRODUCTION OF RENEWABLE GLYCOLATE

(71) Applicant: Massachusetts Institute of Technology, Cambridge, MA (US)

(72) Inventors: Gregory Stephanopoulos, Winchester, MA (US); Zheng-Jun Li, Beijing (CN); Brian Pereira, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/281,994

(22) Filed: Sep. 30, 2016

(65) Prior Publication Data
US 2017/0121717 A1 May 4, 2017

Related U.S. Application Data

(60) Provisional application No. 62/236,234, filed on Oct. 2, 2015.

(51) Int. Cl.
*C12N 15/70* (2006.01)
*C12N 9/00* (2006.01)
*C12P 7/42* (2006.01)
*C12N 9/04* (2006.01)
*C12N 9/02* (2006.01)
*C12N 9/12* (2006.01)
*C12N 9/88* (2006.01)
*C12N 9/90* (2006.01)
*C12N 15/52* (2006.01)

(52) U.S. Cl.
CPC ........... *C12N 15/70* (2013.01); *C12N 9/0006* (2013.01); *C12N 9/0008* (2013.01); *C12N 9/1205* (2013.01); *C12N 9/88* (2013.01); *C12N 9/90* (2013.01); *C12N 15/52* (2013.01); *C12P 7/42* (2013.01); *C12Y 101/01026* (2013.01); *C12Y 102/01021* (2013.01); *C12Y 207/01047* (2013.01); *C12Y 401/02013* (2013.01); *C12Y 401/03001* (2013.01); *C12Y 501/03* (2013.01)

(58) Field of Classification Search
None
See application file for complete search history.

(56) References Cited

FOREIGN PATENT DOCUMENTS

| EP | 2233562 A1 | 9/2010 |
|---|---|---|
| WO | WO 2012/025780 A1 | 3/2012 |
| WO | WO 2013/126721 A1 | 8/2013 |

OTHER PUBLICATIONS

Ishida et al., J. Ferm. and Bioeng., 84 (4): 348-350, 1997 (Year: 1997).*
Izumori et al., Biosci. Biotech. Biochem., 57 (6): 1037-1039, 1993 (Year: 1993).*
Ishida et al., J. Ferm. and Bioeng., 83 (6): 529-534, 1997 (Year: 1997).*
Gustafsson et al., Trends in Biotechnology, 22, 7 :346-353, 2004 (Year: 2004).*
Alkim et al., Optimization of ethylene glycol production from (D)-xylose via a synthetic pathway implemented in *Escherichia coli*. Microb Cell Fact. Sep. 4, 2015;14:127. doi: 10.1186/s12934-0150-312-7.
Alkim et al., The synthetic xylulose-1 phosphate pathway increases production of glycolic acid from xylose-rich sugar mixtures. Biotechnol Biofuels. Sep. 20, 2016;9:201. doi: 10.1186/s13068-016-0610-2. eCollection 2016.
Cam et al., Engineering of a Synthetic Metabolic Pathway for the Assimilation of (d)-Xylose into Value-Added Chemicals. ACS Synth Biol. Jul. 15, 2016;5(7):607-18. doi: 10.1021/acssynbio. 5b00103. Epub Jul. 24, 2015.
Pereira et al., Efficient utilization of pentoses for bioproduction of the renewable two-carbon compounds ethylene glycol and glycolate. Metab Eng. Mar. 2016;34:80-87. doi: 10.1016/j.ymben.2015.12. 004. Epub Dec. 19, 2015.
Ajikumar et al. Isoprenoid pathway optimization for taxol precursor overproduction in *Escherichia coli*. Science 330, 70-74 (2010).
Baldoma et al., Metabolism of L-fucose and L-rhamnose in *Escherichia coli*: aerobic-anaerobic regulation of L-lactaldehyde dissimilation. J. Bacteriol. 170, 416-421 (1988).
Caballero et al., Identification of lactaldehyde dehydrogenase and glycolaldehyde dehydrogenase as functions of the same protein in *Escherichia coli*. J. Biol. Chem. 258, 7788-7792 (1983).
Cesario et al. Enhanced bioproduction of poly-3-hydroxybutyrate from wheat straw lignocellulosic hydrolysates. N. Biotechnol. 31, 104-113 (2014 ).
Chen et al., Metabolic engineering of Corynebacterium glutamicum for the de novo production of ethylene glycol from glucose. Metab. Eng. Advance online publication. doi: 10.1016lj.ymben.2015.10. 013 (2015).
Datsenko et al., One-step inactivation of chromosomal genes in *Escherichia coli* K-12 using PCR products. Proc. Natl. Acad. Sci. U.S.A. 97, 6640-6645 (2000).
Deng et al., Metabolic engineering of *E. coli* for efficient production of glycolic acid from glucose. Biochem. Eng. J. 103, 256-262 (2015).
Hartmanis et al., Diol metabolism and diol dehydratase in Clostridium glycolicum. Arch. Biochem. Biophys. 245, 144-152 (1986).
Itoh et al. Purification and characterization of D-tagatose 3-epimerase from *Pseudomonas* sp. ST-24. Biosci. Biotechnol. Biochem. 58, 2168-2171 (1994).
Ji et al. Catalytic conversion of cellulose into ethylene glycol over supported carbide catalysts. Catal. Today 147, 77-85 (2009).
Kallio et al., An engineered pathway for the biosynthesis of renewable propane. Nat. Commun. 5, 4731 (2014).
Kim et al., Strain engineering of *Saccharomyces cerevisiae* for enhanced xylose metabolism. Biotechnol. Adv. 31, 851-861 (2013).
Koivistoinen et al. Glycolic acid production in the engineered yeasts *Saccharomyces cerevisiae* and Kluyveromyces lactis. Microb. Cell Fact. 12, 82 (2013).

(Continued)

*Primary Examiner* — Nancy A Treptow
(74) *Attorney, Agent, or Firm* — Wolf, Greenfield & Sacks, P.C.

(57) ABSTRACT

Some aspects provide engineered microbes for glycolate production. Methods for microbe engineering and culturing are also provided herein. Such engineered microbes exhibit greatly enhanced capabilities for glycolate production.

18 Claims, 5 Drawing Sheets

Specification includes a Sequence Listing.

(56) References Cited

OTHER PUBLICATIONS

Kurosawa et al., Engineering xylose metabolism in triacylglycerol-producing Rhodococcus opacus for lignocellulosic fuel production. Biotechnol. Biofuels. 6, 134 (2013).

Leblanc et al., Metabolism of D-arabinose: a new pathway in Escherichia coli. J. Bacterial. 106, 90-96 (1971).

Lee et al. Systems metabolic engineering of microorganisms for natural and non-natural chemicals. Nat. Chem. Biol. 8, 536-546 (2012).

Martin et al. A platform pathway for production of 3-hydroxyacids provides a biosynthetic route to 3-hydroxy-y-butyrolactone. Nat. Commun. 4, 1933 (2013).

Nieves et al., Engineering sugar utilization and microbial tolerance toward lignocellulose conversion. Front. Bioeng. Biotechnol. 3, 17 (2015).

Olson et al., Recent progress in consolidated bioprocessing. Curr. Opin. Biotechnol. 23, 396-405 (2012).

Pang et al., Catalytic hydrogenation of corn stalk to ethylene glycol and 1,2-propylene glycol. Ind. Eng. Chem. Res. 50, 6601-6608 (2011).

Pellicer et al., glc locus of Escherichia coli: characterization of genes encoding the subunits of glycolate oxidase and the glc regulator protein. J. Bacterial. 178, 2051-2059 (1996).

Pereira et al., Engineering a novel biosynthetic pathway in Escherichia coli for production of renewable ethylene glycol. Biotechnol Bioeng. Feb. 2016;113(2):376-83. doi: 10.1002/bit.25717. Epub Sep. 18, 2015.

Sun et al., Selective hydrogenolysis of biomass-derived xylitol to ethylene glycol and propylene glycol on supported Ru catalysts. Green Chem. 13, 135-142 (2011).

Wasylenko et al., Metabolomic and 13C-metabolic flux analysis of a xylose-consuming Saccharomyces cerevisiae strain expressing xylose isomerase. Biotechnol. Bioeng. 112, 470-483 (2015).

Xu et al. Modular optimization of multi-gene pathways for fatty acids production in E. coli. Nat. Commun. 4, 1409 (2013).

Yim et al. Metabolic engineering of Escherichia coli for direct production of 1,4-butanediol. Nat. Chem. Biol. 1, 445-452 (2011).

Zahoor et al., Metabolic engineering of Corynebacterium glutamicum for glycolate production. J. Biotechnol. 192, 366-375 (2014).

\* cited by examiner

```
                              SEQUENCE LISTING

<160> NUMBER OF SEQ ID NOS: 40

<210> SEQ ID NO 1
<211> LENGTH: 71
<212> TYPE: DNA
<213> ORGANISM: Artificial Sequence
<220> FEATURE:
<223> OTHER INFORMATION: Synthetic Polynucleotide

<400> SEQUENCE: 1
gagatatata gatgtgaatt atcccccacc cggtcaggca ggggataacg tgtgtaggct     60
ggagctgctt c                                                         71

<210> SEQ ID NO 2
<211> LENGTH: 70
<212> TYPE: DNA
<213> ORGANISM: Artificial Sequence
<220> FEATURE:
<223> OTHER INFORMATION: Synthetic Polynucleotide

<400> SEQUENCE: 2
ggcccggtta tcggtagcga taccgggcat ttttttaagg aacgatcgat catatgaata     60
tcctccttag                                                           70

<210> SEQ ID NO 3
<211> LENGTH: 70
<212> TYPE: DNA
<213> ORGANISM: Artificial Sequence
<220> FEATURE:
<223> OTHER INFORMATION: Synthetic Polynucleotide

<400> SEQUENCE: 3
caatgacaaa ccacacttca taattatcaa aaatcgtcat tatcgtgtcc gtgtaggctg     60
gagctgcttc                                                           70

<210> SEQ ID NO 4
<211> LENGTH: 70
<212> TYPE: DNA
<213> ORGANISM: Artificial Sequence
<220> FEATURE:
<223> OTHER INFORMATION: Synthetic Polynucleotide

<400> SEQUENCE: 4
gcaactctct actgtttctc catacccgtt tttttggatg gagtgaaacg catatgaata     60
tcctccttag                                                           70

<210> SEQ ID NO 5
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 5
gcgcaacttt acctgacgac                                                20

<210> SEQ ID NO 6
<211> LENGTH: 20
```

```
<212> TYPE: DNA
<213> ORGANISM: Artificial Sequence
<220> FEATURE:
<223> OTHER INFORMATION: Synthetic Polynucleotide

<400> SEQUENCE: 6
ttgcccgctt acaaaccgat                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 7
agacgaaaac gaaaagcccg                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 8
ggtgacaggg cgacctaaaa                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 9
taatgtctgt cgcatcccgc                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 10
gctttctcaa aacgggcgag                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 11
atccttcgtt cacagtgggg                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 12
```
gcggttgagt ccactctttc                                         20

<210> SEQ ID NO 13
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 13
agcggtgttg gcgaaataag                                         20

<210> SEQ ID NO 14
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 14
gctccggtta tttccgggat                                         20

<210> SEQ ID NO 15
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 15
gctgccatgg acaaagttgg tatgttctac acc                          33

<210> SEQ ID NO 16
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 16
agtcgtcgac atgagctccg taggccggcc taaacgaatt cttaggccag tttatcacgg    60

<210> SEQ ID NO 17
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 17
ctgcggccgg ccctttaata aggagatata ccatggaacg aaataaactt gc            52

<210> SEQ ID NO 18
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 18
gccggagctc taaacgaatt cttaccaggc ggtatggtaa agc                43

<210> SEQ ID NO 19
<211> LENGTH: 61
<212> TYPE: DNA
<213> ORGANISM: Artificial Sequence
<220> FEATURE:
<223> OTHER INFORMATION: Synthetic Polynucleotide

<400> SEQUENCE: 19
gaattcgttt agagctctaa ataaggagga ataaccatgg tatccggcta tattgcagga    60
g                                                                    61

<210> SEQ ID NO 20
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 20
actggtcgac gctatcttca cacttcctct ataaattc                            38

<210> SEQ ID NO 21
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 21
atgacgattt ttgataatta tgaagtgtgg tttgtcattg cattaattgc gttgcgctca    60
ctg                                                                  63

<210> SEQ ID NO 22
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 22
tgcgagccat ggtatatctc cttattaaag                                     30

<210> SEQ ID NO 23
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 23
cggcgtttag gccggcctta aataaggagg aataaccatg acctttcgca attgtgtcgc    60

<210> SEQ ID NO 24
<211> LENGTH: 64
<212> TYPE: DNA
<213> ORGANISM: Artificial Sequence
<220> FEATURE:
<223> OTHER INFORMATION: Synthetic Polynucleotide

<400> SEQUENCE: 24
ttgatatgtc gacctcgagg cggccgcgag ctctaaacga attcggcctg ttccagttga    60
gtgg                                                                 64

<210> SEQ ID NO 25
<211> LENGTH: 62
<212> TYPE: DNA
<213> ORGANISM: Artificial Sequence
<220> FEATURE:

<223> OTHER INFORMATION: Synthetic Polynucleotide

<400> SEQUENCE: 25
cggccggaat tcgtttagag ctctaaataa ggaggaataa ccatgcaaaa cattactcag    60
tc                                                                  62

<210> SEQ ID NO 26
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 26
taaaggcggc cgctaaacga attcttacag cgccagcgca ctgg                    44

<210> SEQ ID NO 27
<211> LENGTH: 68
<212> TYPE: DNA
<213> ORGANISM: Artificial Sequence
<220> FEATURE:
<223> OTHER INFORMATION: Synthetic Polynucleotide

<400> SEQUENCE: 27
cggccgaatt cgtttagcgg ccgcttaaat aaggaggaat aacgatgatg gctaacagaa    60
tgattctg                                                            68

<210> SEQ ID NO 28
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 28
ggccgctcga gtaaacgaat tcttaccagg cggtatggta aagc                    44

<210> SEQ ID NO 29
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 29
tttaggccgg ccttaaataa ggaggaataa cgatggaacg aaataaactt gctc         54

<210> SEQ ID NO 30
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 30
tatgtcgacc tcgaggcggc cgcgagctct aaacgaattc ttactcttca attcgtaacc    60
cat                                                                 63

<210> SEQ ID NO 31
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 31
tttagagctc ttaaataagg aggaataacc atgttatccg gctatattgc ag                52

<210> SEQ ID NO 32
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 32
tatgcggccg ctaaacgaat tctcacactt cctctataaa ttcag                         45

<210> SEQ ID NO 33
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 33
tttagcggcc gcttaaataa ggaggaataa ccatgtcagt acccgttcaa catc               54

<210> SEQ ID NO 34
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 34
gccgctcgag taaacgaatt cttaagactg taaataaacc acct                          44

<210> SEQ ID NO 35
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 35
ttatagagga agtgtgaaga tagcgagatg gccggcctta aataag                        46

<210> SEQ ID NO 36
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 36
aactcaatga tgatgatgat gatggtaaac gaattcttac agcgc                         45

<210> SEQ ID NO 37
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 37
ttgacagcta gctcagtcct aggtataatg ctagctacta gagaaagagg agaaatatac         60
catggctcga ggtcgacggt atcgata                                             87

<210> SEQ ID NO 38
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 38
ggtgcctaat gagtgagcta actca                                          25

<210> SEQ ID NO 39
<211> LENGTH: 873
<212> TYPE: DNA
<213> ORGANISM: Artificial Sequence
<220> FEATURE:
<223> OTHER INFORMATION: Codon-optimized form of Pseudomonas cichorii
      gene

<400> SEQUENCE: 39
atgaacaaag ttggtatgtt ctacacctac tggagcaccg aatggatggt tgacttccca     60
gcgaccgcca aacgtattgc gggcctgggt ttcgatctga tggaaatctc tctgggcgag    120
ttccataacc tgtctgatgc taaaaagcgt gagctgaaag cggtagcaga cgatctgggt    180
ctgactgtaa tgtgctgtat cggtctgaag tctgaatatg acttcgcaag cccggacaag    240
tccgttcgtg acgctggcac ggaatacgtc aaacgtctgc tggatgactg tcacctgctg    300
ggcgcaccag tgtttgctgg tctgaccttc tgtgcttggc cgcagagccc tccgctggac    360
atgaaggaca acgtccgtta tgttgaccgt gctatcgaga gcgttcgtcg tgttatcaaa    420
gtggcggaag actacggcat catttatgca ctggaagtgg tcaatcgttt cgagcagtgg    480
ctgtgcaacg atgcgaaaga agcaatcgct ttcgcggatg ctgttgactc cccggcttgc    540
aaagtacaac tggacacttt tcacatgaac atcaagaaaa cttctttccg tgatgcgatt    600
ctggcctgca aaggcaaaat gggccacttt cacctgggtg aagcaaaccg tctgccgccg    660
ggtgaaggtc gtctgccgtg ggatgaaatc tttggtgccc tgaaagaaat cggttacgac    720
ggcaccattg tgatggaacc gttcatgcgt aaaggcggtt ctgtgtcccg tgcggtgggt    780
gtttggcgtg atatgtccaa cggtgcaacc gacgaagaga tggatgaacg tgcgcgtcgt    840
tctctgcaat cgtccgtga taaactggcc taa                                 873

<210> SEQ ID NO 40
<211> LENGTH: 537
<212> TYPE: DNA
<213> ORGANISM: Artificial Sequence
<220> FEATURE:
<223> OTHER INFORMATION: Synthetic Polynucleotide

<400> SEQUENCE: 40
taacactagt tcgcagagtg ttatggttta catccttgaa agcctgctgg ataagggttt     60
agcgtaacag aacgttttta cgcggaattg ttcgtaatat gccaaatgac aatttaagaa    120
agtgttctaa tttattagaa atttgcactt aaatcaaaaa gttacggaca attcaaccac    180
caatcaataa attaaagggc acattaaagt acacaatatt tgtgcccttc tctgtttctt    240
tcccgttatc agctagctgg aaactttta tacagagttt agagccctac tccatacgtt    300
tttgatacgc tttgtcgtga ttcacccagc acctgcgcac ctgtggcgcc ggtgatgccg    360
gccacgatgc gtccggcgta gaggatcgag atctcgatcc cgcgaaatta atacgactca    420

```
ctatagggga attgtgagcg gataacaatt cccacggatg gcttgacagc tagctcagtc    480
ctaggtataa tgctagctac tagagaaaga ggagaaatat accatggaca aagttgg      537
```

MICROBIAL PRODUCTION OF RENEWABLE GLYCOLATE

RELATED APPLICATION

This application claims the benefit under 35 U.S.C. § 119(e) of U.S. provisional application No. 62/236,234, filed Oct. 2, 2015, which is incorporated by reference herein in its entirety.

GOVERNMENT SUPPORT

This invention was made with Government support under Grant No. DE-SC0006698 awarded by the Department of Energy. The Government has certain rights in the invention.

FIELD

The production of glycolate through recombinant gene expression and metabolic engineering is disclosed herein.

BACKGROUND

Glycolate, the conjugate base of glycolic acid, is an α-hydroxy acid with applications primarily in skin care and personal care products, but also in dyeing and tanning, as a food additive, as a cleaning agent, and as a precursor for biocompatible polymers. Though glycolic acid is found in natural sources including sugarcane and sugar beet, it is chiefly manufactured from fossil fuels, via the carbonylation of formaldehyde by synthesis gas. In addition to the issues surrounding fossil fuels, there are concerns about formaldehyde being associated with the final glycolic acid product, especially as used in personal care products.

SUMMARY

The present disclosure relates to the development of an alternate process for the bioproduction of renewable glycolate. Direct production of glycolate has been established previously (Koivistoinen et al., 2013; Martin et al., 2013; Zahoor et al., 2014; Cam et al., 2015; Deng et al., 2015); these studies encompass various substrates and organisms, but, with the exception of the work by Cam et al. (2015), all of the studies employ the glyoxylate shunt for glycolate production. As described herein, cleavage of D-xylose can be utilized for glycolate production and that pathway can complement the glyoxylate shunt pathway for very efficient production of glycolate, achieving 0.63 g/g yield.

As is disclosed herein, glycolate can be produced directly from renewable resources. Of biological sources for the generation of glycolate, lignocellulosic biomass is the most abundant. The cellulose and hemicellulose fractions of lignocellulose, or other sources of sugars, can be broken down into two-carbon compounds using engineered microbes that express pathways that enable efficient utilization of pentoses. The engineered microbes can convert these simple sugars into the valuable two-carbon product, glycolate.

According to one aspect, cells engineered to produce glycolate are provided. The cells engineered to produce glycolate in some embodiments have reduced or eliminated activity of, or reduced or eliminated expression of xylulokinase relative to a wild type cell, recombinantly expresses an enzyme that interconverts xylulose and ribulose, recombinantly expresses D-ribulose-phosphate aldolase, recombinantly expresses a D-ribulokinase, and recombinantly expresses a glycolaldehyde dehydrogenase, such as aldehyde dehydrogenase A.

In some embodiments, the cell includes a deletion of the gene encoding xylulokinase. In some embodiments, the xylulokinase is encoded by a xylB gene. In certain embodiments, the xylulokinase is encoded by a xylB gene from *Escherichia coli*.

In some embodiments, the enzyme that interconverts xylulose and ribulose is D-tagatose 3-epimerase. In some embodiments, the D-tagatose 3-epimerase is encoded by a dte gene. In some embodiments, the D-tagatose 3-epimerase is encoded by a dte gene from *Pseudomonas cichorii*. In certain embodiments, D-tagatose 3-epimerase is encoded by the dte gene from *P. cichorii* that is codon-optimized for *E. coli*.

In some embodiments, the D-ribulose-phosphate aldolase is encoded by a fucA gene. In certain embodiments, the D-ribulose-phosphate aldolase is encoded by a fucA gene from *E. coli*.

In some embodiments, the D-ribulokinase is encoded by a fucK gene. In certain embodiments, the D-ribulokinase is encoded by a fucK gene from *E. coli*.

In some embodiments, the glycolaldehyde dehydrogenase is an aldehyde dehydrogenase A, which is encoded by an aldA gene. In certain embodiments, glycolaldehyde dehydrogenase is encoded by an aldA gene from *E. coli*.

In some embodiments, the cell has reduced or eliminated activity of, or reduced or eliminated expression of glycolaldehyde reductase relative to a wild type cell. In certain embodiments, the cell includes a deletion of the gene encoding glycolaldehyde reductase. In some embodiments, the glycolaldehyde reductase is encoded by a fucO gene.

In some embodiments, the cell has reduced or eliminated activity of, or reduced or eliminated expression of glycolate oxidase relative to a wild type cell, optionally reduced or eliminated expression of a subunit of glycolate oxidase. In certain embodiments, the cell includes a deletion of the gene encoding glycolate oxidase or a gene encoding a subunit of glycolate oxidase. In certain embodiments, the subunit of glycolate oxidase is encoded by a glcD gene.

In some embodiments, the cell further recombinantly expresses a glyoxylate reductase. In some embodiments, the glyoxylate reductase is encoded by a ycdW gene. In certain embodiments, the glyoxylate reductase is encoded by a ycdW gene from *E. coli*.

In some embodiments, the cell further recombinantly expresses isocitrate lyase. In some embodiments, the isocitrate lyase is encoded by an aceA gene. In certain embodiments, the isocitrate lyase is encoded by an aceA gene from *E. coli*.

In some embodiments, the cell further recombinantly expresses idh kinase/phosphatase. In some embodiments idh kinase/phosphatase is encoded by an aceK gene. In certain embodiments, the idh kinase/phosphatase is encoded by an aceK gene from *E. coli*. In other embodiments, the cell has reduced or eliminated activity of, or reduced or eliminated expression of isocitrate lyase regulator relative to a wild type cell. In other embodiments, the isocitrate lyase regulator is encoded by an iclR gene. In certain embodiments, the cell includes a deletion of the gene iclR.

In some embodiments, the cell has reduced or eliminated activity of, or reduced or eliminated expression of glyoxylate carboligase relative to a wild type cell. In certain embodiments, the cell includes a deletion of the gene encoding glyoxylate carboligase. In certain embodiments, the glyoxylate carboligase is encoded by a gcl gene.

In some embodiments, the cell has reduced or eliminated activity of, or reduced or eliminated expression of malate synthase A relative to a wild type cell. In certain embodiments, the cell includes a deletion of the gene encoding malate synthase A. In certain embodiments, the malate synthase A is encoded by an aceB gene.

In some embodiments, the cell has reduced or eliminated activity of, or reduced or eliminated expression of malate synthase G relative to a wild type cell. In certain embodiments, the cell includes a deletion of the gene encoding malate synthase G. In certain embodiments, the malate synthase G is encoded by a glcB gene.

In some embodiments, the cell is a bacterial cell. In some embodiments, the cell is an *E. coli* cell.

In some embodiments, the cell is a fungal cell. In some embodiments, the cell is a yeast cell, such as a *Saccharomyces* spp. cell.

According to another aspect, methods of producing glycolate are provided. The method of producing glycolate, in some embodiments, includes culturing any of the cells described herein in the presence of xylose under conditions that result in production of glycolate.

According to another aspect, *E. coli* cells engineered to produce glycolate are provided. In some embodiments, the *E. coli* cell includes a deletion of a xylB gene, recombinantly expresses a dte gene from *Pseudomonas cichorii* that is codon-optimized for *E. coli*, recombinantly expresses a fucA gene from *E. coli*, recombinantly expresses a fucK gene from *E. coli*, and recombinantly expresses an aldA gene from *E. coli*.

In some embodiments, the *E. coli* cell further includes a deletion of a fucO gene. In some embodiments, the *E. coli* cell further includes a deletion of a glcD gene.

In some embodiments, the *E. coli* cell further recombinantly expresses a ycdW gene from *E. coli*. In some embodiments, the *E. coli* cell further recombinantly expresses an aceA gene from *E. coli*.

In some embodiments, the *E. coli* cell further recombinantly expresses an aceK gene from *E. coli*. In some embodiments, the *E. coli* cell has reduced or eliminated activity of, or reduced or eliminated expression of iclR relative to a wild type cell. In certain embodiments, the cell includes a deletion of the gene iclR.

In some embodiments, the *E. coli* cell further includes a deletion of a gcl gene. In some embodiments, the *E. coli* cell further includes a deletion of an aceB gene. In some embodiments, the *E. coli* cell further includes a deletion of a glcB gene.

In some embodiments, one or more of the recombinantly expressed genes are under the control of an inducible promoter. In certain embodiments, the inducible promoter is a T5 promoter. In some embodiments, the inducible promoter is induced by a chemical. In certain embodiments, the chemical is isopropyl β-D-1-thiogalactopyranoside (IPTG) or anhydrotetracycline (aTc).

In some embodiments, one or more of the recombinantly expressed genes are under the control of a constitutive promoter. In certain embodiments, the constitutive promoter is a CP1 promoter.

In yet another aspect, methods of producing glycolate are provided. In some embodiments, the method includes culturing any of the *E. coli* cells described herein in the presence of xylose under conditions that result in the production of glycolate.

The subject matter of this application may involve, in some cases, interrelated products, alternative solutions to a particular problem, and/or a plurality of different uses of a single system or article.

Other advantages, features, and uses will be apparent from the detailed description of certain non-limiting embodiments, the drawings, and the claims.

BRIEF DESCRIPTION OF THE DRAWINGS

FIG. 3A depicts the strains as cultivated in tube cultures containing minimal medium and D-xylose, and final yields were calculated after 48 h. Columns are the average of triplicate experiments, and error bars represent standard deviation. FIG. 3B depicts strain GA-10 and FIG. 3C depicts strain GA-11 as cultivated in batch bioreactors containing minimal medium with D-xylose; cell growth, glycolate concentration, and D-xylose concentration were measured over time.

DETAILED DESCRIPTION OF CERTAIN EMBODIMENTS

Figure 1:
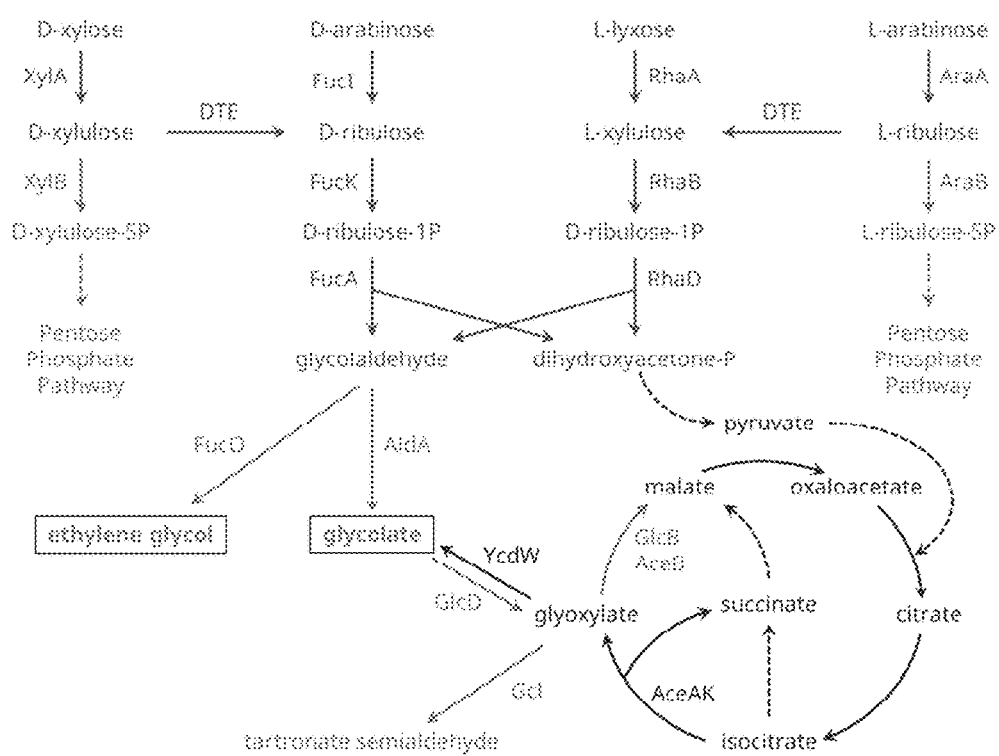
FIG. 1. Metabolic network for production of glycolate from pentoses. Enzymes associated with the reactions are shown. Solid black lines represent reactions and intermediates associated with pentose cleavage into two- and three-carbon intermediates, double gray lines represent conversion of the two-carbon intermediate, and double black lines represent conversion of the three-carbon intermediate. Solid gray lines represent reactions and intermediates in pathways attenuated in specified strains.

The majority of chemicals and fuels today are derived primarily from crude oil, natural gas, and coal, i.e., from fossil fuels, but as concerns about the use of fossil fuels continue to mount, there is a strong impetus to institute alternative, sustainable resources. Biomass, in particular from plants, is one such promising and abundant resource. Exploiting biomass as a feedstock for biobased chemicals and fuels necessitates technology for the conversion of raw plant material into useful products. This conversion can be effected by catalysts in chemical processes (Ji et al., 2009; Pang et al., 2011; Sun and Liu, 2011) and/or by microorganisms in biological processes (Cesário et al., 2014; Olson et al., 2012). Though chemical processes are faster, they generally exhibit low selectivities, thereby requiring greater energy input and greater capital investment; therefore, an effective, single-step biological process with high selectivity has the potential to lead the market. Consequently, there is a critical need to engineer microorganisms that efficiently yield beneficial products from plant-derived substrates.

Current biotechnology chiefly utilizes plant-derived sugar and starch, but future technologies will likely make use of lignocellulosic feedstocks (Nieves et al., 2015). The most abundant constituents of lignocellulose are D-glucose and D-xylose, which are derived principally from cellulose and hemicellulose, respectively. D-Glucose is easily metabolized by most microorganisms, but only a smaller fraction of microorganisms can metabolize D-xylose; for this reason, metabolic engineering research has concentrated on D-glucose as the substrate (Kallio et al., 2014; Lee et al., 2012; Xu et al., 2013; Yim et al., 2011), with significantly fewer studies employing D-xylose (Kim et al., 2013; Kurosawa et al., 2013; Wasylenko and Stephanopoulos, 2015). However, D-xylose is a significant constituent of lignocellulose and can be obtained from biomass at a lower cost; therefore, D-xylose represents an important resource for valorization. Disclosed herein is a scheme by which D-xylose, and other hemicellulose-derived pentoses, can be utilized efficiently for the production of two-carbon products.

Various two-carbon compounds can be produced through biosynthetic pathways branching from central metabolism intermediates. These intermediates are generally three-carbon intermediates, and one carbon is lost for each two-carbon product that is formed; the theoretical yield for such pathways is therefore 2:3 C-mol-product/C-mol-substrate. Alternatively, if D-xylose, instead of being metabolized through the pentose phosphate pathway, is cleaved into two- and three-carbon intermediates and if each intermediate can be subsequently converted into the product, this new approach can yield 4:5 C-mol-product/C-mol-substrate (2:1 mol-product/mol-D-xylose), a significant, 20% improvement. Implementation of this strategy requires pathways for the cleavage of D-xylose into two- and three-carbon intermediates, for transforming the two-carbon intermediate into the target product, and for the conversion of the three-carbon intermediate into product, such as glycolate.

Provided herein is a novel set of pathways that enable glycolate (the conjugate base of glycolic acid) production from various pentoses, including superior titer from D-xylose.

As demonstrated herein, cleavage of D-xylose can be utilized for glycolate production and this pathway can complement the glyoxylate shunt pathway for very efficient production of glycolate.

The development of lignocellulose as a sustainable resource for the production of fuels and chemicals will rely on technology capable of converting the raw materials into useful compounds; some such transformations can be achieved by biological processes employing engineered microorganisms. Towards the goal of valorizing the hemicellulose fraction of lignocellulose, a set of pathways that enable efficient utilization of pentoses for the biosynthesis of notable two-carbon products was designed and validated, as shown herein. These pathways were incorporated into *Escherichia coli*, and engineered strains produced glycolate from a pentose, such as D-xylose. Using D-xylose as the substrate, an engineered strain produced 40 g/L glycolate at a yield of 0.63 g/g, which is the greatest reported yield to date.

The engineered pathways described herein for the production of glycolate in cells involve several enzymatic components.

In some embodiments, a cell engineered to produce glycolate has reduced or eliminated activity of, or reduced or eliminated expression of xylulokinase relative to a wild type cell. In some embodiments, the cell comprises a deletion of the gene encoding xylulokinase (see, e.g., EC:2.7.1.17, HGNC: 12839, Entrez Gene: 9942, Ensembl: ENSG00000093217, OMIM: 604049, UniProtKB: O75191), which converts xylulose to xylulose 5-phosphate. Examples include xylulokinase encoded by a xylB gene. In some embodiments, the xylB gene is from *E. coli*, such as K01996 (Translation: AAA24769.1), X04691 (Translation: CAA28395.1), U00039 (Translation: AAB 18541.1), U00096 (Translation: AAC76588.1), and AP009048 (Translation: BAE77729.1).

In some embodiments, a cell engineered to produce glycolate recombinantly expresses an enzyme that interconverts xylulose and ribulose, such as D-tagatose 3-epimerase (see e.g., EC 5.1.3.31). In some embodiments, the D-tagatose 3-epimerase is encoded by a dte gene, optionally a dte gene from *Pseudomonas cichorii*, such as AB000361 (Translation: BAA24429.1). In some embodiments, the dte gene from *P. cichorii* is codon-optimized for *E. coli*, such as SEQ ID NO: 39.

In some embodiments, a cell engineered to produce glycolate recombinantly expresses D-ribulose-phosphate aldolase (see, e.g., EcoCyc: EG10348, b2800, ECK2795, and UniProtKB: P0AB87, and Entrez gene: 85675619), which can cleave the D-ribulose-1-phosphate to yield glycolaldehyde and dihydroxyacetone phosphate. Examples include D-ribulose-phosphate aldolase encoded by a fucA gene. In some embodiments, the fucA gene is from *E. coli*, such as M31059 (Translation: AAA23823.1), X15025 (Translation: CAA33125.1), U29581 (Translation: AAB40450.1), U00096 (Translation: AAC75842.1), AP009048 (Translation: BAE76872.1), and M27177.

In some embodiments, a cell engineered to produce glycolate recombinantly expresses a D-ribulokinase (see e.g., EC 2.7.1.17, EcoCyc: EG10350, b2803, ECK2798, UniProtKB: P11553, LASV01000160 (Translation: KKA22072.1), LN681231 (Translation: CEK28509.1), JPFO01000018 (Translation: KFE38580.1), CP002038 (Translation: ADM96299.1), AE008918 (Translation: AAL54221.1), CBLX010000009 (Translation: CDG39496.1)), which converts D-ribulose to D-ribulose 5-phosphate. Examples include D-ribulokinase encoded by a fucK gene. In certain embodiments, the fucK gene is from *E. coli*, such as X15025 (Translation: CAA33128.1), U29581 (Translation: AAB40453.1), U00096 (Translation: AAC75845.2), AP009048 (Translation: BAE76875.1).

In some embodiments, a cell engineered to produce glycolate recombinantly expresses a glycolaldehyde dehydrogenase (see e.g., EC 1.2.1.21, EcoCyc: EG10035, b1415, ECK1408, UniProtKB: P25553, CBWM010000577 (Translation: CDL22412.1)), which converts glycolaldehyde to glycolate. Glycoaldehyde dehydrogenase activity may also be effected by promiscuous lactaldehyde dehydrogenase. Examples include glycolaldehyde dehydrogenase encoded by an aldA gene. In certain embodiments, the aldA gene is from *E. coli*, such as M64541 (Translation: AAA23427.1), U00096 (Translation: AAC74497.1) and AP009048 (Translation: BAA15032.1).

In some embodiments, the cell has reduced or eliminated activity of, or reduced or eliminated expression of glycolaldehyde reductase relative to a wild type cell. In some embodiments, the cell comprises a deletion of the gene encoding glycolaldehyde reductase (see e.g., EC 1.1.1.77, UnitProtKB: P0A9S1 and P0A9S2), which converts glycolaldehyde to ethylene glycol. Examples of glycolaldehyde reductases include GldA and FucO. Examples include glycolaldehyde reductase encoded by a fucO gene. In certain embodiments, the fucO gene is from *E. coli*, such as M31059 (Translation: AAA23824.1, X15025 (Translation: CAA33124.1), M27177 (Translation: AAA23825.1), U29581 (Translation: AAB40449.1), U00096 (Translation: AAC75841.2), AP009048 (Translation: BAE76871.1), L07763 (No translation available), AE005174 (Translation: AAG57913.1), BA000007 (Translation: BAB37082.1).

In some embodiments, the cell has reduced or eliminated activity of, or reduced or eliminated expression of glycolate oxidase or a subunit of glycolate oxidase relative to a wild type cell. In some embodiments, the cell comprises a deletion of a gene encoding glycolate oxidase or a subunit thereof (see e.g., Entrez Gene: 54363 and 15112, Ensembl: ENSG00000101323 and ENSMUSG00000027261, UniProtKB: Q9UJM8 and Q9WU19, RefSeq (mRNA): NM_017545 and NM_010403, RefSeq (protein): NP_060015.1 and NP_034533.1, AF320978 (Translation: AAG49357.1)), which converts glycolate to glyoxylate. In some embodiments, the cell comprises a deletion of the gene encoding a subunit of glycolate oxidase. Examples include glycolate oxidase encoded by a HAO1, Gox1, XHD1, glcD, glcE or glcF. In some embodiments, a subunit of glycolate oxidase is encoded by a glcD gene. In certain embodiments, the glcD gene is from *E. coli*, such as JHDN01000063 (Translation: EYE21243.1).

In some embodiments, the cell further recombinantly expresses a glyoxylate reductase (see e.g., EC 1.1.1.26, EC 1.1.1.79, NP_036335.1, UniProtKB: Q9UBQ7, AF134895 (Translation: AAF00111.1), AF146018 (Translation: AAD45886.1), AF146689 (Translation: AAD46517.1), AF113215 (Translation: AAG39286.1), AK026287 (Translation: BAB15430.1), AK315690 (Translation: BAG38053.1), AL158155 (Translation: CAI13848.1), CH471071 (Translation: EAW58284.1), CH471071 (Translation: EAW58285.1), BC000605 (Translation: AAH00605.1), AF113251 (Translation: AAD54066.1), which converts glyoxylate to glycolate, using the cofactor NADH or NADPH. Examples include glyoxylate reductase encoded by ycdW, ghrA, ghrB, GRHOR, grhpra. In some embodiments, glyoxylate reductase is encoded by a ycdW gene. In certain embodiments, the ycdW gene is from *E. coli*, such as U00096 (Translation: AAC74117.2) and AP009048 (Translation: BAA35814.1).

In some embodiments, the cell further recombinantly expresses isocitrate lyase (see e.g., EC 4.1.3.1, UniProtKB: P0A9G6), which converts isocitrate to succinate and glyoxylate. Examples include isocitrate lyase encoded by ICL, aceA, icl1, DDB_G0273017, RHA1_RS 10355, PFL_RS 19805. In some embodiments, isocitrate lyase is encoded by an aceA gene. In certain embodiments, the aceA gene is from *E. coli*, such as X12431 (Translation: CAA30974.1), X07543 (Translation: CAA30416.1), M22621 (Translation: AAC13650.1), U00006 (Translation: AAC43109.1), U00096 (Translation: AAC76985.1), AP009048 (Translation: BAE78017.1), M20714 (Translation: AAA24009.1).

In some embodiments, the cell further recombinantly expresses idh kinase/phosphatase (see e.g., EC 2.7.11.5, UniProtKB: P11071), which catalyzes the phosphorylation/dephosphorylation of the enzyme isocitrate dehydrogenase. In some embodiments, idh kinase/phosphatase is encoded by a aceK gene. In certain embodiments, the aceK gene is from *E. coli*, such as M20714 (Translation: AAA24010.1), M18974 (Translation: AAA24007.1), U00006 (Translation: AAC43110.1), U00096 (Translation: AAC76986.1), AP009048 (Translation: BAE78018.1), M22621 (Translation: AAC13651.1), M63497 (Translation: AAA73005.1). In other embodiments, the cell has reduced or eliminated activity of, or reduced or eliminated expression of isocitrate lyase regulator (NC_000913.3, EG10491, UniProtKB: P16528), which encodes a repressor for the aceBAK operon, relative to a wild type cell. In some embodiments, the cell comprises a deletion of the gene iclR (see e.g., M31761 (Translation: AAA24008.1), M63914 (Translation: AAA50561.1), U00006 (Translation: AAC43112.1), U00096 (Translation: AAC76988.2), AP009048 (Translation: BAE78020.1), M63497 (Translation: AAA73003.1)).

As described above, the aceK gene encodes for idh kinase/phosphatase and expression of aceK from the plasmid results in increased idh kinase/phosphatase expression relative to a wild type cell. In some instances, increased expression of idh kinase/phosphatase can also be achieved by reducing or eliminating the activity of, or reducing or eliminating the expression of iclR. The iclR gene encodes a repressor for the aceBAK operon.

In some embodiments, the cell has reduced or eliminated activity of, or reduced or eliminated expression of glyoxylate carboligase relative to a wild type cell. In some embodiments, the cell comprises a deletion of the gene encoding glyoxylate carboligase (see e.g., EG11583, UniProtKB: P0AEP7), which catalyzes the condensation of glyoxylate to tartronate semialdehyde. In some embodiments, the glyoxylate carboligase is encoded by a gcl gene, such as L03845 (Translation: AAA23864.1), U82664 (Translation: AAB40260.1), U00096 (Translation: AAC73609.1), AP009048 (Translation: BAE76285.1).

In some embodiments, the cell has reduced or eliminated activity of, or reduced or eliminated expression of malate synthase A relative to a wild type cell. In some embodiments, the cell comprises a deletion of the gene encoding malate synthase A (UniProtKB: P08997), which is involved in step 2 of the subpathway that converts isocitrate to (S)-malate. In some embodiments, the malate synthase A is encoded by an aceB gene, such as Ref. Seq.'s NP_418438.1, NC_000913.3, X12431 (Translation: CAA30973.), U00006 (Translation: AAC43108.1), U00096 (Translation: AAC76984.1), AP009048 (Translation: BAE78016.1).

In some embodiments, the cell has reduced or eliminated activity of, or reduced or eliminated expression of malate synthase G relative to a wild type cell. In some embodiments, the cell comprises a deletion of the gene encoding malate synthase G (see e.g., NP_417450.1, NC_000913.3, UniProtKB: P37330), which is involved in step 2 of the subpathway that converts isocitrate to (S)-malate. In certain embodiments, malate synthase G is encoded by a glcB gene, such as X74547 (Translation: CAA52639.1), U28377 (Translation: AAA69143.1), U00096 (Translation: AAC76012.1), AP009048 (Translation: BAE77036.1).

In some embodiments, the genes are expressed as part of an operon. These genes may be placed in any order in the operon. It should be appreciated that some cells may express an endogenous copy of one of more of the aforementioned enzymatic components as well as a recombinant copy.

As one of ordinary skill in the art would be aware, homologous genes for these enzymes can be obtained from other species and can be identified by homology searches, for example through a protein BLAST search, available at the National Center for Biotechnology Information (NCBI) internet site (www.ncbi.nlm.nih.gov). Genes can be cloned, for example by PCR amplification and/or restriction digestion, from DNA from any source of DNA which contains the given gene. In some embodiments, a gene is synthetic. Any means of obtaining or synthesizing a gene encoding for an enzyme can be used.

Also disclosed herein are strategies to optimize production of glycolate from a cell. Optimized production of glycolate refers to producing a higher amount glycolate following pursuit of an optimization strategy than would be achieved in the absence of such a strategy. Optimization of production of glycolate can involve modifying a gene encoding for an enzyme before it is recombinantly expressed in a cell. In some embodiments, such a modification involves codon optimization for expression in a bacterial cell. For example, this includes the use of heterologous genes from various sources whose sequence has been properly modified (including codon optimization) for optimal expression in the host organism. Codon usages for a variety of organisms can be accessed in the Codon Usage Database (kazusa.or.jp/codon/). Codon optimization, including identification of optimal codons for a variety of organisms, and methods for achieving codon optimization, are familiar to one of ordinary skill in the art, and can be achieved using standard methods.

In some embodiments, modifying a gene encoding for an enzyme before it is recombinantly expressed in a cell involves making one or more mutations in the gene encoding for the enzyme before it is recombinantly expressed in a cell. For example, a mutation can involve a substitution or deletion of a single nucleotide or multiple nucleotides. In some embodiments, a mutation of one or more nucleotides in a gene encoding for an enzyme will result in a mutation in the enzyme, such as a substitution or deletion of one or more amino acids.

Additional changes can include increasing copy numbers of the gene components of pathways active in production of glycolate, such as by additional episomal expression. In some embodiments, screening for mutations in components of the production of glycolate, or components of other pathways, that lead to enhanced production of glycolate may be conducted through a random mutagenesis screen, or through screening of known mutations. In some embodiments, shotgun cloning of genomic fragments could be used to identify genomic regions that lead to an increase in production of glycolate, through screening cells or organisms that have these fragments for increased production of glycolate. In some cases one or more mutations may be combined in the same cell or organism.

In some embodiments, production of glycolate in a cell can be increased through manipulation of enzymes that act in the same pathway as the enzymes described herein. For example, in some embodiments it may be advantageous to increase expression of an enzyme or other factor that acts upstream or downstream of a target enzyme such as an enzyme described herein. This could be achieved by overexpressing the upstream or downstream factor using any standard method.

A further strategy for optimization of production of glycolate is to increase expression levels of one or more genes, which can be described as "pathway balancing". This may be accomplished, for example, through selection of appropriate promoters and ribosome binding sites. In some embodiments, the production of glycolate is increased by balancing expression of the genes such as by selecting promoters of various strengths to drive expression of the genes. In some embodiments, this may include the selection of high-copy number plasmids, or low or medium-copy number plasmids. The step of transcription termination can also be targeted for regulation of gene expression, through the introduction or elimination of structures such as stem-loops.

Polypeptides containing mutations or codon optimization of residues as described herein, and isolated nucleic acid molecules encoding such polypeptides. As used herein, the terms "protein" and "polypeptide" are used interchangeably and thus the term polypeptide may be used to refer to a full-length polypeptide and may also be used to refer to a fragment of a full-length polypeptide. As used herein with respect to polypeptides, proteins, or fragments thereof, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may be, but need not be, substantially pure. The term "substantially pure" means that the proteins or polypeptides are essentially free of other substances with which they may be found in production, nature, or in vivo systems to an extent practical and appropriate for their intended use. Substantially pure polypeptides may be obtained naturally or produced using methods described herein and may be purified with techniques well known in the art. Because an isolated protein may be admixed with other components in a preparation, the protein may comprise only a small percentage by weight of the preparation. The protein is nonetheless isolated in that it has been separated from the substances with which it may be associated in living systems, i.e. isolated from other proteins.

Also disclosed herein are nucleic acids that encode for any of the polypeptides described herein, libraries that contain any of the nucleic acids and/or polypeptides described herein, and compositions that contain any of the nucleic acids and/or polypeptides described herein. It should be appreciated that libraries containing nucleic acids or proteins can be generated using methods known in the art. A library containing nucleic acids can contain fragments of genes and/or full-length genes and can contain wild-type sequences and mutated sequences. A library containing proteins can contain fragments of proteins and/or full length proteins and can contain wild-type sequences and mutated sequences. It should be appreciated that codon-optimized forms of any of the nucleic acid and protein sequences described herein can be used in the product and methods disclosed herein.

Any type of cell that can be engineered to recombinantly express genes and/or have reduced or eliminated expression or activity of genes and gene products can be used in the methods, including prokaryotic and eukaryotic cells. In some embodiments the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp. and *Pantoea* spp. The bacterial cell can be a Gram-negative cell such as an *Escherichia coli* (*E. coli*) cell, or a Gram-positive cell such as a species of *Bacillus*. In other embodiments, the cell is a fungal cell such as a yeast cell, e.g., *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp. and industrial polyploid yeast strains. Preferably the yeast strain is a *S. cerevisiae* strain. Other examples of fungi include *Aspergillus* spp., *Penicillium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp. In other embodiments, the cell is an algal cell, or a plant cell.

As disclosed herein and as will be understood by persons skilled in the art, the activity or expression of one or more genes and gene products can be reduced, attenuated or eliminated in several ways, including by reducing expression of the relevant gene, disrupting the relevant gene, introducing one or more mutations in the relevant gene that results in production of a protein with reduced, attenuated or eliminated enzymatic activity, use of specific enzyme inhibitors to reduce, attenuate or eliminate the enzymatic activity, etc.

It should be appreciated that some cells may express an endogenous copy of one or more of the genes disclosed herein as well as a recombinant copy. In some embodiments, if a cell has an endogenous copy of one or more of the genes disclosed herein, then the methods will not necessarily require adding a recombinant copy of the gene(s) that are endogenously expressed. In some embodiments the cell may endogenously express one or more enzymes from the pathways described herein and may recombinantly express one or more other enzymes from the pathways described herein for efficient production of glycolate.

In some embodiments, the terms "overexpression" or "increased expression", as used herein, refers to an increased level of expression of a given gene product in a given cell, cell type or cell state, as compared to a reference cell, for example, a wild type cell of the same cell type or a cell of the same cell type but lacking a specific modification, for example, a genetic modification. Continuous expression of one or more genes that encode D-tagatose 3-epimerase, D-ribulose-phosphate aldolase, D-ribulokinase, and/or glycolaldehyde dehydrogenase in *E. coli* cells engineered to produce glycolate, which results in higher production of glycolate relative to wild type cells, is an example of gene overexpression.

In some embodiments, one or more of the genes disclosed herein is expressed in a recombinant expression vector. In other embodiments, one or more of the genes disclosed herein is expressed as or from one or more chromosomally integrated genes.

As used herein, a "vector" may be any of a number of nucleic acids into which a desired sequence or sequences may be inserted by restriction and ligation for transport between different genetic environments or for expression in a host cell. Vectors are typically composed of DNA, although RNA vectors are also available. Vectors include, but are not limited to: plasmids, fosmids, phagemids, virus genomes and artificial chromosomes.

A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host cell such as a host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

In some embodiments, the native promoter of a gene encoding a gene product conferring a required or desirable phenotype to a microbe, for example, the native promoter of a gene encoding a gene product described herein, is modified in the microbe to alter the regulation of its transcriptional activity. In some embodiments, the modified promoter exhibits an increased transcriptional activity as compared to its unmodified counterpart. The term "modified promoter", as used herein, refers to a promoter the nucleotide sequence of which has been artificially altered. Nucleotide deletion(s), insertion(s) or mutation(s), alone or in combination, are examples of such artificial alterations. Artificial promoter alterations can be effected in a targeted fashion, for example by homologous recombination approaches, such as gene targeting, knockout, knock in, site-directed mutagenesis, or artificial zinc finger nuclease-mediated strategies. Alternatively, such alterations may be effected by a random or quasi-random event, such as irradiation or non-targeted nucleotide integration and subsequent selection. Promoter modifications, in general, are fashioned in order to modulate the transcriptional activation properties of the respective promoter. Methods for the targeted disruption of a native promoter, for example, a native promoter of a gene encoding a gene product described herein, in a microbe, for example, for targeted disruption resulting in an increased transcription rate, are well known to those of skill in the art.

When the nucleic acid molecule that encodes any of the enzymes disclosed herein is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. An example of a constitutive promoter is a CP1 promoter. A variety of conditional or inducible promoters also can be used, such as promoters controlled by the presence or absence of a molecule. An example of a conditional or inducible promoter is the T5 promoter.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors disclosed herein may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA). That heterologous DNA (RNA) is placed under operable control of transcriptional elements to permit the expression of the heterologous DNA in the host cell. Heterologous expression of genes, for production of glycolate, is demonstrated in the Examples using *E. coli*. The novel method for producing glycolate can also be expressed in other bacterial cells, fungi (including yeast cells), plant cells, etc.

A nucleic acid molecule that encodes an enzyme disclosed herein can be introduced into a cell or cells using methods and techniques that are standard in the art. For example, nucleic acid molecules can be introduced by standard protocols such as transformation including chemical transformation and electroporation, transduction, particle bombardment, etc. Expressing the nucleic acid molecule encoding the enzymes also may be accomplished by integrating the nucleic acid molecule into the genome.

Methods of producing glycolate also are provided. The methods of producing glycolate include culturing any of the cells described herein in the presence of a xylose-containing feedstock under conditions that result in production of glycolate.

Microbes such as the engineered bacterial cells described herein can be cultured in media of any type (rich or minimal) and any composition. As would be understood by one of ordinary skill in the art, routine optimization would allow for use of a variety of types of media. The selected medium can be supplemented with various additional components. Some non-limiting examples of supplemental components include one or more carbon sources such as D-arabinose, D-xylose, D-glucose, biomass hydrolysates (specifically hemicellulose) that contains D-xylose, L-arabinose, glycerol and serine; antibiotics; IPTG for gene induction; anhydrotetracycline (aTc) for gene induction; ATCC Trace Mineral Supplement; malonate; cerulenin; and glycolate. Similarly, other aspects of the medium, and growth conditions of the cells disclosed herein may be optimized through routine experimentation. For example, pH and temperature are non-limiting examples of factors which can be optimized. In some embodiments, factors such as choice of media, media supplements, and temperature can influence production levels of glycolate. In some embodiments the concentration and amount of a supplemental component may be optimized. In some embodiments, how often the media is supplemented with one or more supplemental components, and the amount of time that the media is cultured before harvesting glycolate, is optimized.

In some embodiments the temperature of the culture may be between 25 and 43° C., inclusive. For example, it may be 25, 26, 27, 28, 29, 30, 31, 32, 33, 34, 35, 36, 37, 38, 39, 40, 41, 42 or 43° C., or any value in between. In certain embodiments the temperature is between 30 and 32° C. including 30, 31 and 32° C. and any value in between. In certain embodiments the temperature is between 36 and 38° C. including 36, 37 and 38° C. and any value in between. As would be understood by one of ordinary skill in the art, the optimal temperature in which to culture a cell for production of glycolate may be influenced by many factors including the type of cell, the growth media and the growth conditions.

Other non-limiting factors that can be varied through routine experimentation in order to optimize production of glycolate include the concentration and amount of feedstock and any supplements provided, how often the media is supplemented, and the amount of time that the media is cultured before harvesting the glycolate. In some embodiments the cells may be cultured for 0.5, 1, 2, 3, 4, 5, 6, 12, 18, 24, 30, 36, 42, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, including all intermediate values, or greater than 300 hours. In some embodiments optimal production is achieved after culturing the cells for several days such as 3-4 days. However it should be appreciated that it would be routine experimentation to vary and optimize the above-mentioned parameters and other such similar parameters.

Feedstocks for industrial-scale production of three-carbon products and two-carbon products, such as glycolate, include biomass, animal fats, vegetable oils, palm oil, hemp, soy, rapeseed, flax, sunflower, and oleaginous algae. The term "biomass" refers to material produced by growth and/or propagation of a living cell or organism, for example, a microbe. Biomass may contain cells, microbes and/or intracellular contents. An important type of biomass for glycolate production are plant-derived biomass. In some embodiments, biomass for glycolate or glycolate precursor production may comprise plant derived sugars, for example, pentoses.

As disclosed herein, high titers of glycolate are produced through reduced or eliminated activity of, or reduced or eliminated expression of certain gene(s) and the recombinant expression of certain gene(s), in a cell. As used herein "high titer" refers to a titer in the grams per liter (g/L) scale. The titer produced for a given product will be influenced by multiple factors including choice of media. In some embodiments the total glycolate titer is at least 10 g/L (500 milligrams per liter). For example the titer may be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 55, 56, 57, 58, 59, 60, 61, 62, 63, 64, 65, 66, 67, 68, 69, 70, 71, 72, 73, 74, 75, 80, 85, 90, 95, 100, including all intermediate values, or more than 100 g/L.

The liquid cultures used to grow cells can be housed in any of the culture vessels known and used in the art. In some embodiments large scale production in an aerated reaction vessel such as a stirred tank reactor can be used to produce large quantities of glycolate, which can be recovered from the cell culture.

In some embodiments, glycolate production by the engineered cells described herein may be carried out in bioreactors. As used herein, the terms "bioreactor" and "fermentor", which are interchangeably used, refer to an enclosure, or partial enclosure, in which a biological and/or chemical reaction takes place, at least part of which involves a living organism or part of a living organism. A "large-scale bioreactor" or "industrial-scale bioreactor" is a bioreactor that is used to generate a product, for example glycolate, on a commercial or quasi-commercial scale. Large scale bioreactors typically have volumes in the range of liters, hundreds of liters, thousands of liters, or more.

A bioreactor may comprise a microbe or a microbe culture, such as a culture of the engineered cells described herein. In some embodiments, a bioreactor may comprise a spore and/or any kind of dormant cell type of any isolated microbe, for example, in a dry state. In some embodiments, addition of a suitable carbohydrate source to such bioreactors may lead to activation of the dormant cell, for example to germination of a yeast spore, and subsequent conversion of the carbohydrate source, at least in part, to glycolate.

Some bioreactors may include cell culture systems where microbes are in contact with moving liquids and/or gas bubbles. Microbes or microbe cultures may be grown in suspension or attached to solid phase carriers. Non-limiting examples of carrier systems include microcarriers (e.g., polymer spheres, microbeads, and microdisks that can be porous or non-porous), cross-linked beads (e.g., dextran) charged with specific chemical groups (e.g., tertiary amine groups), 2D microcarriers including cells trapped in nonporous polymer fibers, 3D carriers (e.g., carrier fibers, hollow fibers, multicartridge reactors, and semi-permeable membranes that can comprising porous fibers), microcarriers having reduced ion exchange capacity, encapsulation cells, capillaries, and aggregates. Carriers can be fabricated from materials such as dextran, gelatin, glass, and cellulose.

Industrial-scale processes may be operated in continuous, semi-continuous or non-continuous modes. Non-limiting examples of operation modes are batch, fed batch, extended batch, repetitive batch, draw/fill, rotating-wall, spinning flask, and/or perfusion mode of operation.

In some embodiments, bioreactors may be used that allow continuous or semi-continuous replenishment of the substrate stock, for example a carbohydrate source and/or continuous or semi-continuous separation of the product, from the reactor.

Non-limiting examples of bioreactors include: stirred tank fermentors, bioreactors agitated by rotating mixing devices, chemostats, bioreactors agitated by shaking devices, airlift fermentors, packed-bed reactors, fixed-bed reactors, fluidized bed bioreactors, bioreactors employing wave induced agitation, centrifugal bioreactors, roller bottles, and hollow fiber bioreactors, roller apparatuses (for example benchtop, cart-mounted, and/or automated varieties), vertically-stacked plates, spinner flasks, stirring or rocking flasks, shaken multiwell plates, MD bottles, T-flasks, Roux bottles, multiple-surface tissue culture propagators, modified fermentors, and coated beads (e.g., beads coated with serum proteins, nitrocellulose, or carboxymethyl cellulose to prevent cell attachment).

Bioreactors and fermentors may, optionally, comprise a sensor and/or a control system to measure and/or adjust reaction parameters. Non-limiting examples of reaction parameters are: biological parameters, for example growth rate, cell size, cell number, cell density, cell type, or cell state, chemical parameters, for example pH, redox-potential, concentration of reaction substrate and/or product, concentration of dissolved gases, such as oxygen concentration and $CO_2$ concentration, nutrient concentrations, metabolite concentrations, glycolate concentration, xylose concentration, glucose concentration, glutamine concentration, pyruvate concentration, apatite concentration, concentration of an oligopeptide, concentration of an amino acid, concentration of a vitamin, concentration of a hormone, concentration of an additive, serum concentration, ionic strength, concentration of an ion, relative humidity, molarity, osmolarity, concentration of other chemicals, for example buffering agents, adjuvants, or reaction by-products, physical/mechanical parameters, for example density, conductivity, degree of agitation, pressure, and flow rate, shear stress, shear rate, viscosity, color, turbidity, light absorption, mixing rate, conversion rate, as well as thermodynamic parameters, such as temperature, light intensity/quality, etc.

Sensors able to measure parameters as described herein are well known to those of skill in the relevant mechanical and electronic arts. Control systems able to adjust the parameters in a bioreactor based on the inputs from a sensor as described herein are well known to those of skill in the art of bioreactor engineering.

The function and advantage of these and other embodiments will be more fully understood from the examples below. The following examples are intended to illustrate the benefits of the present invention, but do not exemplify the full scope of the invention. Accordingly, it will be understood that the example section is not meant to limit the scope of the invention.

EXAMPLES

Materials and Methods
Strains and Plasmids

*Escherichia coli* K-12 MG1655 (DE3) ΔrecA ΔendA was used as the parent for all strain engineering, and *E. coli* K-12 MG1655 (DE3) ΔrecA ΔendA ΔaldA was constructed previously (Pereira et al., 2015). Site-directed chromosomal deletions were introduced by homologous recombination according to established methods (Datsenko and Wanner, 2000). For deletion of xylB and araB genes, linear DNA for homologous recombination was generated by PCR-amplifying the FRT-flanked antibiotic resistance cassette from pKD4 and pKD3, respectively; the corresponding primer pairs were KOxylB_P1 & KOxylB_P2 and KOaraB_P1 & KOaraB_P2 (see Table 1 for all oligonucleotide sequences). For deletion of fucO, glcD, gcl, aceB, and glcB genes, strains containing these disruptions were purchased from The *Coli* Genetic Stock Center (Yale University, New Haven, Conn.), and linear DNA was generated by PCR-amplifying the corresponding genomic DNA using KOgene_fw & KOgene_rv primer pairs. The various modified strains were used as production hosts. *E. coli* NEB 5-alpha (NEB, Ipswich, Mass., USA) was used for plasmid maintenance.

TABLE 1

Oligonucleotides used in this study.

| Oligonucleotide Name | SEQ ID NO | Sequence (5'-) |
| --- | --- | --- |
| KOxylB_P1 | 1 | GAGATATATAGATGTGAATTATCCCCCACCCGGTCAGGC AGGGGATAACGTGTGTAGGCTGGAGCTGCTTC |
| KOxylB_P2 | 2 | GGCCCGGTTATCGGTAGCGATACCGGGCATTTTTTTAAG GAACGATCGATCATATGAATATCCTCCTTAG |
| KOaraB_P1 | 3 | CAATGACAAACCACACTTCATAATTATCAAAAATCGTCA TTATCGTGTCCGTGTAGGCTGGAGCTGCTTC |
| KOaraB_P2 | 4 | GCAACTCTCTACTGTTTCTCCATACCCGTTTTTTTGGAT GGAGTGAAACGCATATGAATATCCTCCTTAG |
| KOfucO_fw | 5 | GCGCAACTTTACCTGACGAC |
| KOfucO_rv | 6 | TTGCCCGCTTACAAACCGAT |
| KOglcD_fw | 7 | AGACGAAAACGAAAAGCCCG |
| KOglcD_rv | 8 | GGTGACAGGGCGACCTAAAA |
| KOgcl_fw | 9 | TAATGTCTGTCGCATCCCGC |
| KOgcl_rv | 10 | GCTTTCTCAAAACGGGCGAG |
| KOaceB_fw | 11 | ATCCTTCGTTCACAGTGGGG |
| KOaceB_rv | 12 | GCGGTTGAGTCCACTCTTTC |
| KOglcB_fw | 13 | AGCGGTGTTGGCGAAATAAG |
| KOglcB_rv | 14 | GCTCCGGTTATTTCCGGGAT |
| Pc.dte_fw | 15 | GCTGCCATGGACAAAGTTGGTATGTTCTACACC |
| Pc.dte_rv | 16 | AGTCGTCGACATGAGCTCCGTAGGCCGGCCTAAACGAAT TCTTAGGCCAGTTTATCACGG |
| fucA_fw1 | 17 | CTGCGGCCGGCCCTTTAATAAGGAGATATACCATGGAAC GAAATAAACTTGC |
| fucO_rv1 | 18 | GCCGGAGCTCTAAACGAATTCTTACCAGGCGGTATGGTA AAGC |
| fucK_fw1 | 19 | GAATTCGTTTAGAGCTCTAAATAAGGAGGAATAACCATG GTATCCGGCTATATTGCAGGAG |
| fucK_rv1 | 20 | ACTGGTCGACGCTATCTTCACACTTCCTCTATAAATTC |
| T7_fw | 21 | ATGACGATTTTTGATAATTATGAAGTGTGGTTTGTCATT GCATTAATTGCGTTGCGCTCACTG |
| T7_rv | 22 | TGCGAGCCATGGTATATCTCCTTATTAAAG |
| rhaB_fw1 | 23 | CGGCGTTTAGGCCGGCCTAAATAAGGAGGAATAACCAT GACCTTTCGCAATTGTGTCGC |
| rhaB_rv | 24 | TTGATATGTCGACCTCGAGGCGGCCGCGAGCTCTAAACG AATTCGGCCTGTTCCAGTTGAGTGG |
| rhaD_fw | 25 | CGGCCGGAATTCGTTTAGAGCTCTAAATAAGGAGGAATA ACCATGCAAAACATTACTCAGTC |
| rhaD_rv1 | 26 | TAAAGGCGGCCGCTAAACGAATTCTTACAGCGCCAGCGC ACTGG |
| fucO_fw | 27 | CGGCCGAATTCGTTTAGCGGCCGCTTAAATAAGGAGGAA TAACGATGATGGCTAACAGAATGATTCTG |
| fucO_rv2 | 28 | GGCCGCTCGAGTAAACGAATTCTTACCAGGCGGTATGGT AAAGC |
| fucA_fw2 | 29 | TTTAGGCCGGCCCTTTAATAAGGAGGAATAACGATGGAAC GAAATAAACTTGCTC |

TABLE 1-continued

Oligonucleotides used in this study.

| Oligonucleotide Name | SEQ ID NO | Sequence (5'-) |
|---|---|---|
| fucA_rv | 30 | TATGTCGACCTCGAGGCGGCCGCGAGCTCTAAACGAATTCTTACTCTTCAATTCGTAACCCAT |
| fucK_fw2 | 31 | TTTAGAGCTCTTAAATAAGGAGGAATAACCATGTTATCCGGCTATATTGCAG |
| fucK_rv2 | 32 | TATGCGGCCGCTAAACGAATTCTCACACTTCCTCTATAAATTCAG |
| aldA_fw | 33 | TTTAGCGGCCGCTTAAATAAGGAGGAATAACCATGTCAGTACCCGTTCAACATC |
| aldA_rv | 34 | GCCGCTCGAGTAAACGAATTCTTAAGACTGTAAATAAACCACCT |
| rhaB_fw2 | 35 | TTATAGAGGAAGTGTGAAGATAGCGAGATGGCCGGCCTTAAATAAG |
| rhaD_rv2 | 36 | AACTCAATGATGATGATGATGATGGTAAACGAATTCTTACAGCGC |
| MCS2_fw | 37 | TTGACAGCTAGCTCAGTCCTAGGTATAATGCTAGCTACTAGAGAAAGAGGAGAAATATACCATGGCTCGAGGTCGACGGTATCGATA |
| MCS2_rv | 38 | GGTGCCTAATGAGTGAGCTAACTCA |

Plasmid construction and DNA manipulations were performed following standard molecular cloning protocols, and all associated enzymes were purchased from NEB. The D-tagatose 3-epimerase gene from *Pseudomonas cichorii* (Pc.dte) (Ishida et al., 1997) was codon optimized for *E. coli* (SEQ ID NO:39) and synthesized by Bio Basic Inc. (Markham, Ontario, Canada). From the synthesized template, Pc.dte was PCR-amplified using primers Pc.dte_fw & Pc.dte_rv, and using primers fucA_fw1 & fucO_rv1 and fucK_fw1 & fucK_rv1, fucA-fucO and fucK, respectively, were amplified from *E. coli* K-12 MG1655 genomic DNA. The PCR products were digested with NcoI/SacI, FseI/SacI, and SacI/Sa/I, respectively; these digested fragments were successively cloned into the NcoI/Sa/I site of p10_T5 (Ajikumar et al., 2010), FseI/SacI site of p10_T5-Pc.dte, and the SacI/Sa/I site of p10_T5-Pc.dte-fucA-fucO, yielding p10_T5-Pc.dte-fucA-fucO-fucK. Next, p5_T5-Pc.dte-fucA-fucO-fucK was constructed by subcloning the XbaI/AccIII fragment of p10_T5-Pc.dte-fucA-fucO-fucK into the XbaI/AccIII site of p5_T7 (Ajikumar et al., 2010).

D-tagatose 3-epimerase enzyme gene and gene product sequences are well known to those of skill in the art. Exemplary, representative gene and gene product sequences include:

Codon-optimized *Pseudomonas cichorii* D-tagatose 3-epimerase (Pc.dte)

Nucleotide sequence (SEQ ID NO: 39):
ATGAACAAAGTTGGTATGTTCTACACCTACTGGAGCACCGAATGGATGGT

TGACTTCCCAGCGACCGCCAAACGTATTGCGGGCCTGGGTTTCGATCTGA

TGGAAATCTCTCTGGGCGAGTTCCATAACCTGTCTGATGCTAAAAAGCGT

GAGCTGAAAGCGGTAGCAGACGATCTGGGTCTGACTGTAATGTGCTGTAT

CGGTCTGAAGTCTGAATATGACTTCGCAAGCCCGGACAAGTCCGTTCGTG

ACGCTGGCACGGAATACGTCAAACGTCTGCTGGATGACTGTCACCTGCTG

GGCGCACCAGTGTTTGCTGGTCTGACCTTCTGTGCTTGGCCGCAGAGCCC

TCCGCTGGACATGAAGGACAAACGTCCGTATGTTGACCGTGCTATCGAGA

GCGTTCGTCGTGTTATCAAAGTGGCGGAAGACTACGGCATCATTTATGCA

CTGGAAGTGGTCAATCGTTTCGAGCAGTGGCTGTGCAACGATGCGAAAGA

AGCAATCGCTTTCGCGGATGCTGTTGACTCCCCGGCTTGCAAAGTACAAC

TGGACACTTTTCACATGAACATCGAAGAAACTTCTTTCCGTGATGCGATT

CTGGCCTGCAAAGGCAAATGGGCCACTTTCACCTGGGTGAAGCAAACCG

TCTGCCGCCGGGTGAAGGTCGTCTGCCGTGGGATGAAATCTTTGGTGCCC

TGAAAGAAATCGGTTACGACGGCACCATTGTGATGGAACCGTTCATGCGT

AAAGGCGGTTCTGTGTCCCGTGCGGTGGGTGTTTGGCGTGATATGTCCAA

CGGTGCAACCGACGAAGAGATGGATGAACGTGCGCGTCGTTCTCTGCAAT

TCGTCCGTGATAAACTGGCCTAA

In order to construct p5_T7-Pc.dte, the T7 promoter was amplified from p10_T7 (Ajikumar et al., 2010) using primers T7_fw & T7_rv, digested with MluI/NcoI, and cloned into the MluI/NcoI site of p5_T5-Pc.dte. From *E. coli* genomic DNA, rhaB, rhaD, and fucO were amplified using primers rhaB_fw1 & rhaB_rv, rhaD_fw & rhaD_rv1, and fucO_fw & fucO_rv2, respectively. The PCR products were digested with FseI/SalI, SacI/NotI, and NotI/XhoI, respectively; the digested fragments were successively cloned into the FseI/SalI site of p5_T7-Pc.dte, the SacI/NotI site of p5_T7-Pc.dte-rhaB, and the NotI/XhoI site of p5_T7-Pc.dte-rhaB-rhaD, yielding p5_T7-Pc.dte-rhaB-rhaD-fucO. Plasmid p5_T5-Pc.dte-fucA-fucO-fucK-rhaB-rhaD was constructed by first PCR-amplifying rhaB-rhaD from p5_T7-

Pc.dte-rhaB-rhaD-fucO using primers rhaB_fw2 & rhaD_rv2 and digesting p5_T5-Pc.dte-fucA-fucO-fucK with SalI; these products were combined using Gibson assembly (Gibson et al., 2009; Gibson et al., 2010).

Furthermore, from *E. coli* genomic DNA, fucA, fucK, and aldA were amplified using primers fucA_fw2 & fucA_rv, fucK_fw2 & fucK_rv2, and aldA_fw & aldA_fw, respectively. The PCR products were digested with FseI/SalI, SacI/NotI, and NotI/XhoI, respectively; the digested fragments were successively cloned into the FseI/SalI site of p5_T5-Pc.dte-fucA-fucO-fucK, the SacI/NotI site of p5_T5-Pc.dte-fucA, and the NotI/XhoI site of p5_T5-Pc.dte-fucA-fucK, yielding p5_T5-Pc.dte-fucA-fucK-aldA. To replace the T5 promoter with a constitutive one, we searched the Registry of Standard Biological Parts (parts.igem.org), and we selected the strongest member of a family of constitutive promoters, part BBa_J23119, herein designated as CP1. A 537-bp DNA fragment (SEQ ID NO: 40) containing SpeI-CP1-RBS-NcoI was synthesized; the synthesized fragment was digested with SpeI/NcoI and used to replace the 1699-bp XbaI-NcoI DNA fragment of p5_T5-Pc.dte-fucA-fucK-aldA by digestion and ligation, giving p5_CP1-Pc.dte-fucA-fucK-aldA.

Constitutive promoter sequences are well known to those of skill in the art. An exemplary, representative sequence is provided below. However, it will be understood that the invention is not limited in this respect.

Exemplary 537-bp DNA fragment containing SpeI-CP1 promotor-RBS-NcoI

```
Nucleotide sequence (SEQ ID NO: 40):
TAACACTAGTTCGCAGAGTGTTATGGTTTACATCCTTGAAAGCCTGCTGG

ATAAGGGTTTAGCGTAACAGAACGTTTTTACGCGGAATTGTTCGTAATAT

GCCAAATGACAATTTAAGAAAGTGTTCTAATTTATTAGAAATTTGCACTT

AAATCAAAAAGTTACGGACAATTCAACCACCAATCAATAAATTAAAGGGC

ACATTAAAGTACACAATATTTGTGCCCTTCTCTGTTTCTTTCCCGTTATC

AGCTAGCTGGAAACTTTTTATACAGAGTTTAGAGCCCTACTCCATACGTT

TTTGATACGCTTTGTCGTGATTCACCCAGCACCTGCGCACCTGTGGCGCC

GGTGATGCCGGCCACGATGCGTCCGGCGTAGAGGATCGAGATCTCGATCC

CGCGAAATTAATACGACTCACTATAGGGGAATTGTGAGCGGATAACAATT

CCCACGGATGGCTTGACAGCTAGCTCAGTCCTAGGTATAATGCTAGCTAC

TAGAGAAAGAGGAGAAATATACCATGGACAAAGTTGG
```

The plasmid, pHHD-ycdW-aceA-aceK (Martin et al., 2013), was generously shared by Prof. Kristala Prather (MIT). The 5.0-kb DNA fragment amplified from pBBR1MCS-2 (Kovach et al., 1995) using primers MCS2_fw & MCS2_rv was purified and self-ligated to generate pMCS-CP1, harboring the constitutive promoter CP1. The ycdW-aceA-aceK fragment was isolated from pHHD-ycdW-aceA-aceK by EcoRI/BamHI digestion and then cloned into pMCS-CP1 digested with the same enzymes to generate the constitutive expression plasmid pMCS-ycdW-aceA-aceK. The myriad plasmids were transformed into the various hosts to give production strains; the relevant plasmids and strains are summarized in Table 2.

TABLE 2

Select plasmids and strains used in this study.

| Name | Description |
|---|---|
| | Plasmids |
| pEGx | p5_T5-Pc.dte-fucA-fucO-fucK |
| pEGa | p5_T7-Pc.dte-rhaB-rhaD-fucO |
| pEGxa | p5_T5-Pc.dte-fucA-fucO-fucK-rhaB-rhaD |
| pGAx1 | p5_T5-Pc.dte-fucA-fucK-aldA |
| pGAx2 | pHHD-ycdW-aceA-aceK |
| pGAx3 | p5_CP1-Pc.dte-fucA-fucK-aldA |
| pGAx4 | pMCS-ycdW-aceA-aceK |
| | Strains |
| WT | *E. coli* K-12 MG1655 (DE3) ΔendA ΔrecA |
| ΔaldA | WT ΔaldA |
| EG-X | WT ΔxylB ΔaldA/pEGx |
| EG-A | WT ΔaraB ΔaldA/pEGa |
| EG-XA | WT ΔxylB ΔaraB ΔaldA/pEGxa |
| GA-01 | WT ΔxylB/pGAx1 |
| GA-02 | WT ΔxylB ΔfucO/pGAx1 |
| GA-03 | WT ΔxylB ΔglcD/pGAx1 |
| GA-04 | WT ΔxylB ΔfucO ΔglcD/pGAx1 |
| GA-05 | WT ΔxylB ΔglcD/pGAx1/pGAx2 |
| GA-06 | WT ΔxylB ΔglcD Δgcl/pGAx1/pGAx2 |
| GA-07 | WT ΔxylB ΔglcD ΔaceB/pGAx1/pGAx2 |
| GA-08 | WT ΔxylB ΔglcD ΔglcB/pGAx1/pGAx2 |
| GA-09 | WT ΔxylB ΔglcD ΔaceB ΔglcB/pGAx1/pGAx2 |
| GA-10 | WT ΔxylB ΔglcD ΔaceB ΔglcB Δgcl/pGAx1/pGAx2 |
| GA-11 | WT ΔxylB ΔglcD ΔaceB ΔglcB Δgcl/pGAx3/pGAx4 |

Media and Cultivation Conditions

Chemicals were purchased from Sigma-Aldrich (St. Louis, Mo., USA) unless otherwise stated. Strain construction and fermentation seed-cultures were performed in lysogeny broth (LB), which was prepared per instructions (BD, NJ, USA). Experiments conducted in tubes (50-mL capped, conical centrifuge tubes) or shake flasks (250-mL flasks) utilized minimal medium (MM1) comprising 2.0 g/L $NH_4Cl$, 5.0 g/L $(NH_4)_2SO_4$, 3.0 g/L $KH_2PO_4$, 7.3 g/L $K_2HPO_4$, 8.4 g/L MOPS, 0.5 g/L NaCl, 2 mL/L 1M $MgSO_4$, 1 mL/L mineral solution, 0.1 mL/L 4 mM $Na_2MoO_4$, and specified sugar; pH was adjusted to 7 with 6 M KOH. The mineral solution consisted of 3.6 g/l $FeCl_2.4H_2O$, 5.0 g/l $CaCl_2.2H_2O$, 1.3 g/l $MnCl_2.2H_2O$, 0.38 g/l $CuCl_2.2H_2O$, 0.50 g/l $CoCl_2.6H_2O$, 0.94 g/l $ZnCl_2$, 0.031 g/l $H_3BO_3$, 0.40 g/l $Na_2EDTA.2H_2O$, and 1.0 g/l thiamine-HCl. Bioreactor fermentations were carried out in a 3-L Bioflo culture vessel (New Brunswick, Conn., USA) with a 2-L working volume. These fermentations utilized minimal medium (MM2) consisting of 2.0 g/L $NH_4Cl$, 5.0 g/L $(NH_4)_2SO_4$, 2.0 g/L $KH_2PO_4$, 0.5 g/L NaCl 2 mL/L 1M $MgSO_4$, 1 mL/L mineral solution, 0.1 mL/L 4 mM $Na_2MoO_4$, and specified sugar; additionally, silicone antifoaming B emulsion was used to prevent foaming Aerobic conditions were maintained by sparging air at 0.5 or 1 L/min, and the pH was maintained at 7.0 with 6 N NaOH. For all cultures, 50 mg/L spectinomycin, 34 mg/L chloramphenicol, and 50 mg/L kanamycin were added as appropriate. To induce gene expression, 0.1 mM IPTG (Zymo Research, Irvine, Calif., USA) and/or 250 μg/L aTc were added.

To assess glycolate production, strains were first grown in LB at 37° C., 250 rpm o/n. These cultures were used to inoculate to 1% v/v 10-mL tube cultures containing MM1 with 10 g/L D-xylose. The tubes were cultivated at 37° C., 250 rpm for strains GA-01, GA-02, GA-03, and GA-04, and at 30° C., 250 rpm for strains GA-05, GA-06, GA-07, GA-08, GA-09, and GA-10. For batch bioreactor production of glycolate from D-xylose, an initial culture of strain GA-03, GA-10, or GA-11 was grown in LB at 37° C., 250 rpm o/n. This culture was used to inoculate to 1% v/v two 50-mL flask cultures of MM1 with 15 g/L D-glucose. After growing o/n at 37° C., 250 rpm, these seed cultures were combined and used to inoculate to 5% v/v a bioreactor containing MM2 with D-xylose; the initial D-xylose concentration was approximately 110 g/L for GA-03 and 65 g/L for GA-10 and GA-11. Temperature was maintained at 37° C. for strain GA-03 and 30° C. for strains GA-10 and GA-11. Dissolved oxygen content was maintained at 20% by altering agitation from 200 to 800 rpm.

Analytical Methods

Culture samples were taken at several times throughout the experiments. Cell growth was assayed by measuring optical densities at 600 nm (Ultrospec 2100 pro, Amersham (GE Healthcare), NJ, USA). Metabolites in the culture supernatants were analyzed in an Agilent 1200 Infinity series HPLC system (Agilent, CA, USA). Analytes were separated by an Aminex HPX-87H column (Bio-Rad, CA, USA) and measured by a refractive index detector. The column was heated to 50° C., and a mobile phase of 14 mM $H_2SO_4$ was run at 0.7 mL/min Concentrations of arabinose, lyxose, xylose, ethylene glycol, glycolate, and other metabolites were calculated based on standard curves.

Example 1

Production of Glycolate from D-xylose Using the Two-Carbon Intermediate

Studies of *E. coli* K-12 metabolism have found that D-arabinose is metabolized by the same enzymes that degrade L-fucose (LeBlanc and Mortlock, 1971). These enzymes, FucI, fucK, and FucA, effect the cleavage of L-fucose into lactaldehyde and dihydroxyacetone phosphate (DHAP) and the cleavage of D-arabinose into glycolaldehyde and DHAP. While lactaldehyde is oxidized to lactate by AldA under aerobic conditions, it is reduced to propanediol by FucO under anaerobic conditions (Baldomà et al., 1988). AldA catalyzes the oxidation of glycolaldehyde into glycolate (Caballero et al., 1983).

D-xylose is the most abundant pentose, so glycolate production from D-xylose is significantly more beneficial. In *E. coli* K-12, D-xylose is metabolized first by isomerization to D-xylulose followed by phosphorylation to D-xylulose-5-phosphate which then continues through the pentose phosphate pathway. Instead of exploring a means to cleave one of these intermediates, an enzyme was sought that could connect the pathway for D-xylose metabolism to that for D-arabinose metabolism. In 1993, Izumori et al. identified an enzyme from *Pseudomonas cichorii* that catalyzes the epimerization of D-tagatose (Izumori et al., 1993); this D-tagatose epimerase (DTE) was also found to interconvert xylulose and ribulose (Itoh et al., 1994; Izumori et al., 1993), so it was hypothesized that DTE can be used to enable D-xylose to proceed into the D-arabinose degradation pathway and thereby yield glycolate.

Figure 2:
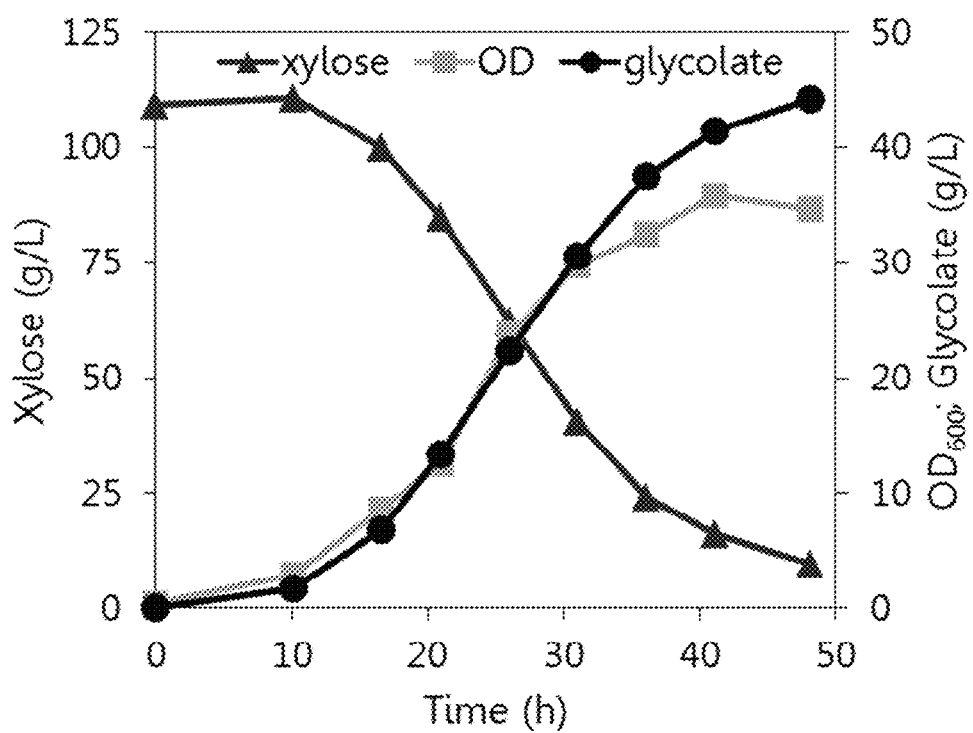
FIG. 2. Production of glycolate using the two-carbon pathway. Strain GA-03 was cultivated on minimal medium with D-xylose in a batch bioreactor; cell growth, glycolate concentration, and D-xylose concentration were measured over time.
Figure 4:
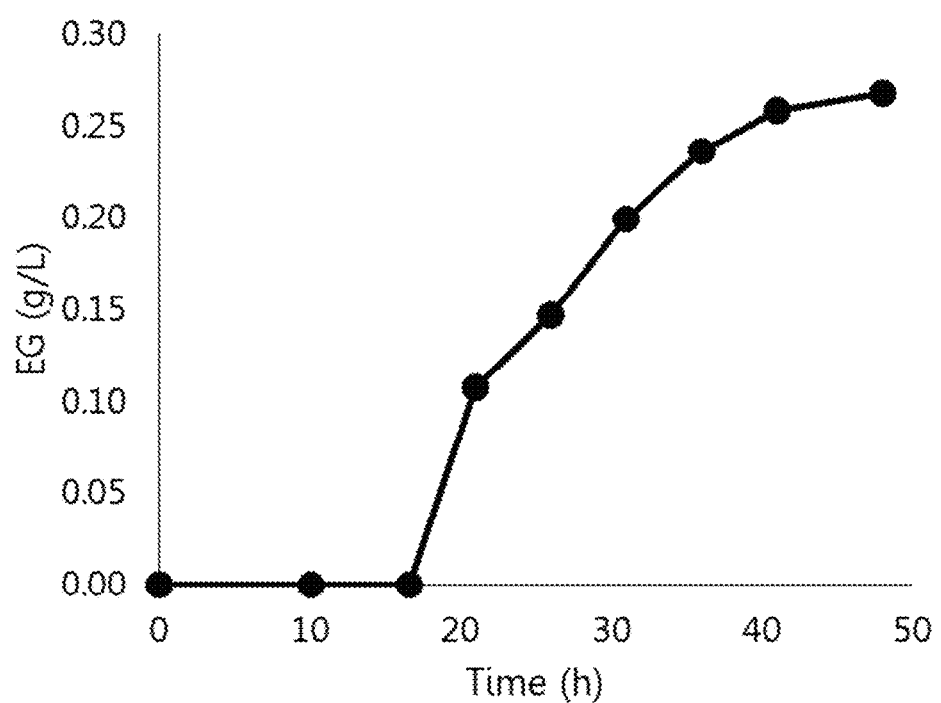
FIG. 4. Byproduct ethylene glycol (EG) formation during glycolate biosynthesis. Strain GA-03 was cultivated on minimal medium with D-xylose in a batch bioreactor; EG concentration was measured over time.

Glycolate is a valuable product, so glycolate production was pursued, focusing on D-xylose as the substrate. *E. coli* K-12 ΔxylB was used as the host background, and to this strain additional modifications were made. In one strain, the fucO gene was deleted in order to prevent glycolaldehyde reduction while in another strain glcD, which encodes a subunit of glycolate oxidase, was deleted to prevent oxidation of glycolate to glyoxylate; there is also a strain in which both genes are knocked out. These host strains were used to overexpress a p5 plasmid comprising Pc.dte, fucA, fucK, and aldA, yielding strains GA-01, GA-02, GA-03, and GA-04. When the four strains were cultivated in D-xylose, glycolate production was observed for all of them, validating the glycolate-biosynthesis pathway (Table 3). Deletion of fucO had little effect on the final glycolate titer, but deletion of glcD resulted in significant improvement. Based on these results, strain GA-03 was selected for scale-up; the strain was grown in a bioreactor with an initial batch of D-xylose. Nearly 100 g/L D-xylose was consumed within 48 h, and the glycolate titer reached 44 g/L, corresponding to a yield of 0.44 g/g (theoretical pathway yield is 0.50 g/g) and a productivity of 0.92 g/(L*h) (FIG. 2); moreover, there was very little ethylene glycol (EG) byproduct formed despite the strain not having fucO deleted (FIG. 4). In this strain, only the two-carbon fraction of D-xylose was utilized; additional utilization of the three-carbon fraction further improves the yield of glycolate.

TABLE 3

Glycolate titer and yield after 48 h of cultivation on minimal medium with D-xylose. Data are averages of triplicate experiments, and errors represent standard deviation (errors less than 0.01 not specified)

| Strain | Glycolate Titer (g/L) | Yield (g-glycolate/g-D-xylose) |
|---|---|---|
| GA-01 | 2.14 ± 0.03 | 0.26 |
| GA-02 | 2.16 ± 0.07 | 0.26 ± 0.01 |
| GA-03 | 3.43 ± 0.02 | 0.46 |
| GA-04 | 3.58 ± 0.06 | 0.47 ± 0.01 |

Example 2: Production of Glycolate from D-xylose Using Both Two-Carbon and Three-Carbon Intermediates The effectiveness of the pathways for pentose cleavage and for product biosynthesis from the consequent two-carbon intermediate was shown above, but for full utilization of a pentose, there also needs to be a pathway for product biosynthesis from the three-carbon intermediate. In the designed metabolic network, the initial three-carbon intermediate is DHAP, which is metabolized through central metabolism. Because glycolate production via the glyoxylate shunt has been established, this complementary glycolate-biosynthesis pathway was adopted to demonstrate efficient pentose use. A plasmid (generously provided by Prof. Kristala Prather, MIT) comprising the pathway genes ycdW, aceA, and aceK, was incorporated into strain GA-03, yielding new strain GA-05, and GA-05 was grown in a 10-mL culture of minimal medium with D-xylose as the carbon source. Glycolate was produced at a yield of 0.52 g/g (FIG. 3A), exceeding the yield for GA-03 (Table 3), which only utilized the two-carbon pathway for glycolate biosynthesis, and thus confirming the concerted activity of both pathways.

Figure 3A:
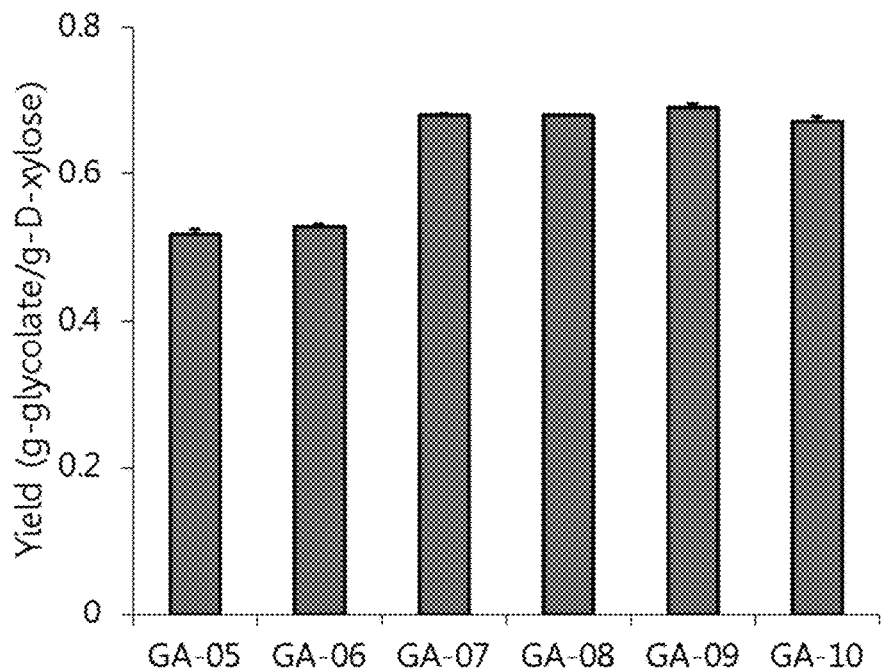
FIGS. 3A-3C. Production of glycolate using both two-carbon and three-carbon pathways.

In an effort to further improve the yield, loss of glyoxylate through side reactions was reduced. The gene gcl encodes glyoxylate carboligase which catalyzes the condensation of two glyoxylate molecules to give tartronate semialdehyde, and the genes aceB and glcB each encode an isozyme of malate synthase, which catalyzes the reaction between glyoxylate and acetyl-CoA. Some or all of these genes were deleted as further modifications to the glycolate-producing strain, and the performance of these new strains was evaluated (FIG. 3A). Deletion of gcl (strain GA-06) had little effect while the yield was significantly increased by deletion of either aceB or glcB (strains GA-07 and GA-08, respectively), though combination of the gene deletions did not further improve the yield. Hence, strain GA-10 was used for scale up studies.

Figure 3B:
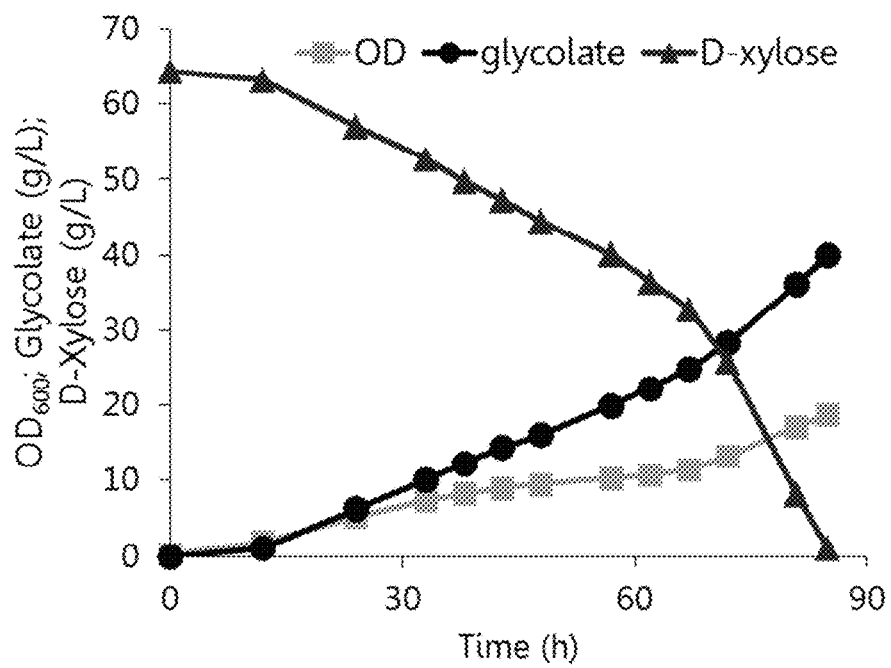
Figure 3C:
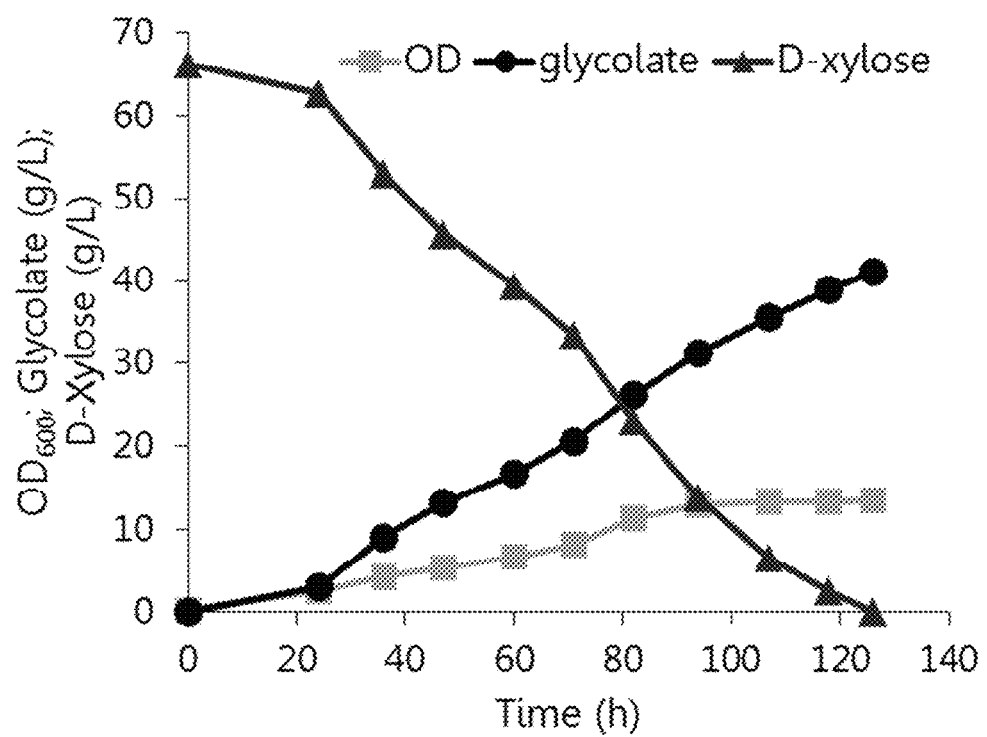

Production of glycolate by strain GA-10 was scaled up by cultivating it in a bioreactor. A single batch of approximately 65 g/L D-xylose was used as the substrate, and all D-xylose was consumed after 85 h (FIG. 3B). From this amount of D-xylose, the strain produced 40 g/L glycolate, corresponding to a yield of 0.63 g/g (theoretical pathway yield is 1.0 g/g); compared to the two-carbon pathway alone, the combination of two- and three-carbon pathways generated approximately the same titer while increasing the yield by roughly 40%. This is a remarkable advance toward the efficient use of hemicellulose, but the use of inducer molecules, isopropyl β-D-1-thiogalactopyranoside (IPTG) and anhydrotetracycline (aTc), could be cost prohibitive for an industrial process; therefore, the system was adapted to instead use constitutive promoters. For both plasmids, the promoters were each changed to a constitutive promoter, namely CP1. These new plasmids were incorporated into new strain GA-11 which was then cultivated in a batch bioreactor. Similar levels of glycolate production were realized, achieving 41 g/L glycolate and a yield of 0.62 g/g without the use of inducer molecules (FIG. 3C). These metrics are encouraging for an industrial process, and they exemplify high-efficiency use of D-xylose for the production of a two-carbon compound.

Lignocellulosic biomass is an abundant, sustainable resource that can be utilized as raw material for the production of chemicals and fuels, and whereas lignin and cellulose are recalcitrant, the hemicellulose fraction is more easily degraded; the resulting hydrolysate is rich in pentoses, primarily D-xylose, and can serve as a meaningful feedstock for bioprocesses. To demonstrate the valorization of such pentoses, a metabolic network by which several pentoses are first cleaved into glycolaldehyde and DHAP was designed and implemented. Because glycolaldehyde production is directly coupled to pentose metabolism, subsequent single-step conversion to glycolate occurs at very high yield. Validated by such positive results, this approach could be extended to efficiently produce other two-carbon compounds. Glycolaldehyde itself can be a desirable product, and targeted production would be a matter of attenuating both oxidation and reduction. Oxidation of glycolate by glycolate oxidase (GlcD, GlcE, and GlcF subunits) can be exploited to give glyoxylate (Pellicer et al., 1996). Moreover, ethylene glycol can be converted by diol dehydratase to acetaldehyde (Hartmanis and Stadtman, 1986), which can then be transformed into ethanol, acetate, or acetyl-CoA. For any of these products, or still others, this strategy and metabolic network provides a good foundation for complementary biosynthetic pathways.

The other three carbons of the substrate pentose enter central metabolism as DHAP, and from central metabolism, they can be diverted to the above-mentioned glycolate, glyoxylate, ethanol, and acetate, but also to many other products derived from central metabolism. These myriad pathways can be used for efficient co-production of different compounds; as a proof of concept, glyoxylate-derived glycolate has been produced at a yield of 0.17 g/g (data not shown). However, the greatest value will likely come from focused production of a single product. For glycolate, the engineered strains disclosed herein were able to cleave D-xylose and effectively use both the two-carbon and three-carbon fractions. Although the use of D-xylose for glycolate production has been reported previously, the yield reached a maximum of 0.45 g/g (Cam et al., 2015) because only the two-carbon fraction was utilized; from D-glucose, the greatest yield is 0.52 g/g (Deng et al., 2015). The engineered strains described herein have surpassed these metrics, achieving 0.63 g-glycolate/g-xylose. Therefore, the engineered cells described herein represent an encouraging demonstration of a single-step bioprocess for the production of renewable glycolate and establishes a set of pentose-specific pathways that can be adapted for efficient production of two-carbon compounds.

REFERENCES

Ajikumar, P. K. et al. Isoprenoid pathway optimization for taxol precursor overproduction in *Escherichia coli*. *Science* 330, 70-74 (2010).

Baldomà, L., Aguilar, J. Metabolism of L-fucose and L-rhamnose in *Escherichia coli*: aerobic-anaerobic regulation of L-lactaldehyde dissimilation. *J. Bacteriol.* 170, 416-421 (1988).

Caballero, E., Baldomà, L., Ros, J., Boronat, A., Aguilar, J. Identification of lactaldehyde dehydrogenase and glycolaldehyde dehydrogenase as functions of the same protein in *Escherichia coli*. *J. Biol. Chem.* 258, 7788-7792 (1983).

Cam, Y. et al. Engineering of a synthetic metabolic pathway for the assimilation of (D)-xylose into value-added chemicals. *ACS Synth Biol*. Advance online publication. doi: 10.1021/acssynbio.5b00103 (2015).

Cesário, M. T. et al. Enhanced bioproduction of poly-3-hydroxybutyrate from wheat straw lignocellulosic hydrolysates. *N. Biotechnol.* 31, 104-113 (2014).

Chen, Z., Huang, J., Wu, Y., Liu, D. Metabolic engineering of *Corynebacterium glutamicum* for the de novo production of ethylene glycol from glucose. *Metab. Eng.* Advance online publication. doi: 10.1016/j.ymben.2015.10.013 (2015).

Datsenko, K. A., Wanner, B. L. One-step inactivation of chromosomal genes in *Escherichia coli* K-12 using PCR products. *Proc. Natl. Acad. Sci. U.S.A.* 97, 6640-6645 (2000).

Deng, Y., Mao, Y., Zhang, X. J. Metabolic engineering of *E. coli* for efficient production of glycolic acid from glucose. *Biochem. Eng. J.* 103, 256-262 (2015).

Gibson, D. G. et al. Enzymatic assembly of DNA molecules up to several hundred kilobases. *Nat. Methods* 6, 343-345 (2009).

Gibson, D. G., Smith, H. O., Hutchison, C. A., 3rd, Venter, J. C., Merryman, C. Chemical synthesis of the mouse mitochondrial genome. *Nat. Methods* 7, 901-903 (2010).

Hartmanis, M. G. N., Stadtman, T. C. Diol metabolism and diol dehydratase in *Clostridium glycolicum*. *Arch. Biochem. Biophys.* 245, 144-152 (1986).

Ishida, Y., Kamiya, T., Itoh, H., Kimura, Y., Izumori, K. Cloning and characterization of the D-tagatose 3-epimerase gene from *Pseudomonas cichorii* ST-24. *J. Ferment. Bioeng.* 83, 529-534 (1997).

Itoh, H. et al. Purification and characterization of D-tagatose 3-epimerase from *Pseudomonas* sp. ST-24. *Biosci. Biotechnol. Biochem.* 58, 2168-2171 (1994).

Izumori, K., Khan, A. R., Okaya, H., Tsumura, T. A new enzyme, D-ketohexose 3-epimerase, from *Pseudomonas* sp. ST-24. *Biosci. Biotechol. Biochem.* 57, 1037-1039 (1993).

Ji, N. et al. Catalytic conversion of cellulose into ethylene glycol over supported carbide catalysts. *Catal. Today* 147, 77-85 (2009).

Kallio, P., Pásztor, A., Thiel, K., Akhtar, M. K., Jones, P. R. An engineered pathway for the biosynthesis of renewable propane. *Nat. Commun.* 5, 4731 (2014).

Kim, S. R., Park, Y. C., Jin, Y. S., Seo, J. H. Strain engineering of *Saccharomyces cerevisiae* for enhanced xylose metabolism. *Biotechnol. Adv.* 31, 851-861 (2013).

Koivistoinen, O. M. et al. Glycolic acid production in the engineered yeasts *Saccharomyces cerevisiae* and *Kluyveromyces lactis*. *Microb. Cell Fact.* 12, 82 (2013).

Kovach, M. E. et al. Four new derivatives of the broad-host-range cloning vector pBBR1MCS, carrying different antibiotic-resistance cassettes. Gene 166, 175-176 (1995).

Kurosawa, K., Wewetzer, S. J., Sinskey, A. J. Engineering xylose metabolism in triacylglycerol-producing *Rhodococcus opacus* for lignocellulosic fuel production. *Biotechnol. Biofuels.* 6, 134 (2013).

LeBlanc, D. J., Mortlock, R. P. Metabolism of D-arabinose: a new pathway in *Escherichia coli*. *J. Bacteriol.* 106, 90-96 (1971).

Lee, J. W. et al. Systems metabolic engineering of microorganisms for natural and non-natural chemicals. *Nat. Chem. Biol.* 8, 536-546 (2012).

Liu, H. et al. Biosynthesis of ethylene glycol in *Escherichia coli*. *Appl. Microbiol. Biotechnol.* 97, 3409-3417 (2013).

Martin, C. H. et al. A platform pathway for production of 3-hydroxyacids provides a biosynthetic route to 3-hydroxy-γ-butyrolactone. *Nat. Commun.* 4, 1933 (2013).

Nieves, L. M., Panyon, L. A., Wang, X. Engineering sugar utilization and microbial tolerance toward lignocellulose conversion. *Front. Bioeng. Biotechnol.* 3, 17 (2015).

Olson, D. G., McBride, J. E., Shaw, A. J., Lynd, L. R. Recent progress in consolidated bioprocessing. *Curr. Opin. Biotechnol.* 23, 396-405 (2012).

Pang, J., Zheng, M., Wang, A., Zhang, T. Catalytic hydrogenation of corn stalk to ethylene glycol and 1,2-propylene glycol. *Ind. Eng. Chem. Res.* 50, 6601-6608 (2011).

Pellicer, M. T., Badía J., Aguilar J., Baldomà, L. glc locus of *Escherichia coli*: characterization of genes encoding the subunits of glycolate oxidase and the glc regulator protein. *J. Bacteriol.* 178, 2051-2059 (1996).

Sun, J., Liu, H. Selective hydrogenolysis of biomass-derived xylitol to ethylene glycol and propylene glycol on supported Ru catalysts. *Green Chem.* 13, 135-142 (2011).

Wasylenko, T. M., Stephanopoulos, G. Metabolomic and $^{13}C$-metabolic flux analysis of a xylose-consuming *Saccharomyces cerevisiae* strain expressing xylose isomerase. Biotechnol. Bioeng. 112, 470-483 (2015).

Xu, P. et al. Modular optimization of multi-gene pathways for fatty acids production in *E. coli*. *Nat. Commun.* 4, 1409 (2013).

Yim, H. et al. Metabolic engineering of *Escherichia coli* for direct production of 1,4-butanediol. *Nat. Chem. Biol.* 7, 445-452 (2011).

Zahoor, A., Otten, A., Wendisch, V. F. Metabolic engineering of *Corynebacterium glutamicum* for glycolate production. *J. Biotechnol.* 192, 366-375 (2014).

All publications, patents and sequence database entries mentioned in the specification herein are hereby incorporated by reference in their entirety as if each individual publication or patent was specifically and individually indicated to be incorporated by reference. In case of conflict, the present application, including any definitions herein, will control.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. An *Escherichia coli* cell engineered to produce glycolate, wherein the cell comprises a deletion of a xylB gene, recombinantly expresses a dte gene from *Pseudomonas cichorii* that is codon-optimized for *E. coli*, recombinantly expresses a fucA gene from *E. coli*, recombinantly expresses a fucK gene from *E. coli*, recombinantly expresses an aldA gene from *E. coli*, and recombinantly expresses a ycdW gene from *E. coli*,
wherein one or more of the recombinantly expressed genes are under the control of one or more promoters,
wherein the one or more promoters is not a native promoter, and
wherein the cell has higher production of glycolate relative to a wild type cell.

2. An *Escherichia coli* cell engineered to produce glycolate,
wherein the cell comprises a deletion of a xylB gene, recombinantly expresses a dte gene from *Pseudomonas cichorii* that is codon-optimized for *E. coli*, recombinantly expresses a fucA gene from *E. coli*, recombinantly expresses a fucK gene from *E. coli*, and recombinantly expresses an aldA gene from *E. coli*,
wherein the cell further comprises a deletion of a fucO gene.

3. The *Escherichia coli* cell of claim 2, wherein the cell further comprises a deletion of a glcD gene.

4. The *Escherichia coli* cell of claim 1, wherein the cell further recombinantly expresses an aceA gene from *E. coli*.

5. The *Escherichia coli* cell of claim 1, wherein the cell further recombinantly expresses an aceK gene from *E. coli*, or wherein the cell has reduced or eliminated activity of, or reduced or eliminated expression of isocitrate lyase regulator relative to a wild type cell.

6. The *Escherichia coli* cell of claim 2, wherein the cell further comprises a deletion of a gcl gene and/or a aceB gene and/or a glcB gene.

7. The *Escherichia coli* cell of claim 3, wherein the cell further comprises a deletion of a fucO gene.

8. The *Escherichia coli* cell of claim 6, wherein the cell further comprises a deletion of an aceB gene.

9. The *Escherichia coli* cell of claim 8, wherein the cell further comprises a deletion of a gcl gene.

10. The *Escherichia coli* cell of claim 1, wherein the promoter is a modified promoter.

11. The *Escherichia coli* cell of claim 1, wherein the promoter is a constitutive promoter.

12. The *Escherichia coli* cell of claim 11, wherein the constitutive promoter is a CP1 promoter.

13. The *Escherichia coli* cell of claim 1, wherein the promoter is a conditional or inducible promoter.

14. The *Escherichia coli* cell of claim 13, wherein the inducible promoter is a T5 promoter.

15. The *Escherichia coli* cell of claim 1, wherein one or more of the recombinantly expressed genes is expressed in a recombinant expression vector.

16. The *Escherichia coli* cell of claim 1, wherein one or more of the recombinantly expressed genes is expressed from one or more chromosomally integrated genes.

17. The *Escherichia coli* cell of claim 2, wherein the cell produces about 0.63 grams of glycolate per gram of substrate.

18. The *Escherichia coli* cell of claim 2, wherein the dte gene from *Pseudomonas cichorii* comprises a sequence of SEQ ID NO: 39.

* * * * *